United States Patent
Kraus et al.

(10) Patent No.: US 11,311,011 B2
(45) Date of Patent: *Apr. 26, 2022

(54) CONTINUOUS ON-LINE ADJUSTABLE DISINFECTANT/SANITIZER/BLEACH GENERATOR

(71) Applicant: ECOLAB USA INC., Saint Paul, MN (US)

(72) Inventors: Paul R. Kraus, Saint Paul, MN (US); Thomas C. Rustad, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 92 days.

This patent is subject to a terminal disclaimer.

(21) Appl. No.: 16/232,681

(22) Filed: Dec. 26, 2018

(65) Prior Publication Data

US 2019/0124922 A1 May 2, 2019

Related U.S. Application Data

(60) Continuation of application No. 15/836,368, filed on Dec. 8, 2017, now Pat. No. 10,201,156, which is a
(Continued)

(51) Int. Cl.
*A61L 9/00* (2006.01)
*A01N 37/16* (2006.01)
(Continued)

(52) U.S. Cl.
CPC ............. *A01N 37/16* (2013.01); *A01N 37/02* (2013.01); *A01N 59/00* (2013.01); *A61L 2/18* (2013.01);
(Continued)

(58) Field of Classification Search
CPC ...... A01N 1/0215; A01N 27/00; A01N 53/00; A61L 2/00; A61L 2/186; B05C 3/00; B05C 5/00; B05D 1/00; B08B 3/14
(Continued)

(56) References Cited

U.S. PATENT DOCUMENTS 2,448,252 A   8/1948   Cornthwaite et al.
2,955,905 A   10/1960  Davies et al.
(Continued)

FOREIGN PATENT DOCUMENTS

CA   2475361 A1   8/2003
EP   0231632 A2   8/1987
(Continued)

OTHER PUBLICATIONS

Yin, De Lu (Tyler), "Switching catalysis from hydrolysis to perhydrolysis in P. fluorescens esterase", Biochemistry, (2010) vol. 49, pp. 1931-1942. Mar. 9, 2011.
(Continued)

*Primary Examiner* — Monzer R Chorbaji
(74) *Attorney, Agent, or Firm* — McKee, Voorhees & Sease PLC

(57) ABSTRACT

Methods and systems for on-site, continuous generation of peracid chemistry, namely peroxycarboxylic acids and peroxycarboxylic acid forming compositions, are disclosed. In particular, an adjustable biocide formulator or generator system is designed for on-site generation of peroxycarboxylic acids and peroxycarboxylic acid forming compositions from sugar esters. Methods of using the in situ generated peroxycarboxylic acids and peroxycarboxylic acid forming compositions are also disclosed.

20 Claims, 8 Drawing Sheets

Related U.S. Application Data continuation of application No. 15/154,283, filed on May 13, 2016, now Pat. No. 9,861,101, which is a continuation of application No. 14/479,886, filed on Sep. 8, 2014, now Pat. No. 9,365,509, which is a division of application No. 13/330,981, filed on Dec. 20, 2011, now Pat. No. 8,858,895.

(60) Provisional application No. 61/427,951, filed on Dec. 29, 2010.

(51) Int. Cl.
| | | |
|---|---|---|
| *C02F 1/50* | (2006.01) | |
| *A01N 59/00* | (2006.01) | |
| *B01J 4/00* | (2006.01) | |
| *C07C 407/00* | (2006.01) | |
| *B01J 19/00* | (2006.01) | |
| *A61L 2/24* | (2006.01) | |
| *C07C 409/24* | (2006.01) | |
| *A61L 2/18* | (2006.01) | |
| *B01J 19/24* | (2006.01) | |
| *B01J 14/00* | (2006.01) | |
| *C02F 1/72* | (2006.01) | |
| *A01N 37/02* | (2006.01) | |
| *C02F 103/08* | (2006.01) | |

(52) U.S. Cl.
CPC ............... *A61L 2/186* (2013.01); *A61L 2/24* (2013.01); *B01J 4/001* (2013.01); *B01J 4/008* (2013.01); *B01J 14/00* (2013.01); *B01J 19/0006* (2013.01); *B01J 19/0013* (2013.01); *B01J 19/24* (2013.01); *C02F 1/50* (2013.01); *C02F 1/722* (2013.01); *C07C 407/00* (2013.01); *C07C 409/24* (2013.01); *A61L 2202/14* (2013.01); *B01J 2219/00049* (2013.01); *B01J 2219/00121* (2013.01); *B01J 2219/00159* (2013.01); *B01J 2219/24* (2013.01); *C02F 2103/08* (2013.01)

(58) Field of Classification Search
USPC ...... 424/76.8; 134/56 R, 186.21; 422/28, 32, 422/300, 255–256, 261; 252/186.42, 252/186.21; 562/2, 4, 6; 222/52, 71, 222/129; 221/191, 206; 206/439
See application file for complete search history.

(56) References Cited

U.S. PATENT DOCUMENTS

| | | | |
|---|---|---|---|
| 3,256,198 | A | 6/1966 | Matzner |
| 3,272,750 | A | 9/1966 | Chase |
| 3,432,546 | A | 3/1969 | Oringer et al. |
| 3,847,830 | A | 11/1974 | Williams et al. |
| 3,925,234 | A | 12/1975 | Hachmann et al. |
| 4,003,841 | A | 1/1977 | Hachmann et al. |
| 4,051,058 | A | 9/1977 | Bowing et al. |
| 4,126,573 | A | 11/1978 | Johnston |
| 4,170,453 | A | 10/1979 | Kitko |
| 4,233,235 | A | 11/1980 | Camden et al. |
| 4,370,251 | A | 1/1983 | Liao et al. |
| 4,412,934 | A | 11/1983 | Chung et al. |
| 4,483,778 | A | 11/1984 | Thompson et al. |
| 4,486,327 | A | 12/1984 | Murphy et al. |
| 4,617,090 | A | 10/1986 | Chum et al. |
| 4,655,781 | A | 4/1987 | Hsieh et al. |
| 4,778,618 | A | 10/1988 | Fong et al. |
| 4,964,870 | A | 10/1990 | Fong et al. |
| 5,030,240 | A | 7/1991 | Wiersema et al. |
| 5,122,538 | A | 6/1992 | Lokkesmoe et al. |
| 5,143,641 | A | 9/1992 | Nunn |
| 5,200,189 | A | 4/1993 | Oakes et al. |
| 5,314,687 | A | 5/1994 | Oakes et al. |
| 5,431,849 | A | 7/1995 | Damhus et al. |
| 5,503,765 | A | 4/1996 | Schepers et al. |
| 5,505,740 | A | 4/1996 | Kong et al. |
| 5,616,335 | A | 4/1997 | Nicolle et al. |
| 5,637,755 | A | 6/1997 | Nagumo et al. |
| 5,716,923 | A | 2/1998 | MacBeath |
| 5,718,910 | A | 2/1998 | Oakes et al. |
| 5,827,447 | A | 10/1998 | Tamura et al. |
| 5,827,808 | A | 10/1998 | Appleby et al. |
| 5,977,403 | A | 11/1999 | Byers |
| 5,998,350 | A | 12/1999 | Burns et al. |
| 6,022,381 | A | 2/2000 | Dias et al. |
| 6,177,393 | B1 | 1/2001 | McGregor et al. |
| 6,207,108 | B1* | 3/2001 | Carr ............... A01N 37/16 252/186.38 |
| 6,207,632 | B1 | 3/2001 | Brooker et al. |
| 6,211,237 | B1 | 4/2001 | Huss et al. |
| 6,221,341 | B1 | 4/2001 | Montgomery |
| 6,284,719 | B1 | 9/2001 | Simms |
| 6,399,564 | B1 | 6/2002 | Speed et al. |
| 6,569,286 | B1 | 5/2003 | Withenshaw et al. |
| 6,599,871 | B2 | 7/2003 | Smith |
| 6,602,845 | B2 | 8/2003 | Connor et al. |
| 6,649,140 | B2 | 11/2003 | Paparatto et al. |
| 6,689,732 | B1 | 2/2004 | Guedira et al. |
| 7,012,154 | B2 | 3/2006 | Vineyard et al. |
| 7,547,421 | B2* | 6/2009 | McSherry ............ C07C 407/00 422/424 |
| 7,569,232 | B2 | 8/2009 | Man et al. |
| 7,598,218 | B2 | 10/2009 | Stolte et al. |
| 7,915,445 | B2 | 3/2011 | Maata et al. |
| 7,919,122 | B2* | 4/2011 | Okano ............... C07C 407/00 424/616 |
| 8,075,857 | B2 | 12/2011 | McSherry et al. |
| 8,802,061 | B2 | 8/2014 | Tichy et al. |
| 8,828,910 | B2 | 9/2014 | Aksela et al. |
| 8,877,254 | B2 | 11/2014 | Li et al. |
| 8,877,354 | B2 | 11/2014 | Horiuchi et al. |
| 9,044,403 | B2 | 6/2015 | Schultz |
| 9,192,909 | B2 | 11/2015 | Kraus et al. |
| 9,271,494 | B2 | 3/2016 | Pedersen et al. |
| 9,365,509 | B2* | 6/2016 | Kraus ............... B01J 4/008 |
| 10,201,156 | B2* | 2/2019 | Kraus ............... C07C 409/24 |
| 2003/0100469 | A1 | 5/2003 | Connor et al. |
| 2003/0192130 | A1* | 10/2003 | Kaaret ............... D06M 13/285 8/115.51 |
| 2005/0008526 | A1 | 1/2005 | Bianchetti et al. |
| 2006/0019864 | A1* | 1/2006 | Muller ............... C11D 1/83 510/506 |
| 2006/0173209 | A1 | 8/2006 | Vineyard et al. |
| 2006/0177518 | A1 | 8/2006 | Stevenson et al. |
| 2007/0249712 | A1 | 10/2007 | Dee et al. |
| 2007/0274857 | A1* | 11/2007 | Okano ............... A01N 59/00 422/28 |
| 2008/0176784 | A1 | 7/2008 | Clowes et al. |
| 2009/0018049 | A1 | 1/2009 | Stolte et al. |
| 2009/0208365 | A1 | 8/2009 | McSherry et al. |
| 2009/0314652 | A1 | 12/2009 | Buschmann et al. |
| 2010/0084603 | A1 | 4/2010 | Narayan et al. |
| 2011/0168567 | A1 | 7/2011 | Smith et al. |
| 2011/0169270 | A1 | 7/2011 | Todorof |
| 2011/0171062 | A1 | 7/2011 | Wolfe |
| 2011/0172897 | A1 | 7/2011 | Schneider |
| 2011/0177145 | A1 | 7/2011 | Erkenbrecher, Jr. et al. |
| 2012/0172437 | A1 | 7/2012 | Kraus et al. |
| 2012/0322872 | A1 | 12/2012 | Kraus et al. |
| 2013/0203849 | A1 | 8/2013 | Ben Yehuda |
| 2015/0018319 | A1 | 1/2015 | Larson et al. |

FOREIGN PATENT DOCUMENTS

| | | |
|---|---|---|
| EP | 0267047 A2 | 5/1988 |
| EP | 0269435 A2 | 6/1988 |
| EP | 1022946 B1 | 9/1998 |
| EP | 1131016 B1 | 11/1999 |
| EP | 1125497 A2 | 2/2001 |
| EP | 1435203 A1 | 7/2004 |

(56) References Cited

FOREIGN PATENT DOCUMENTS

| | | |
|---|---|---|
| JP | 62155203 | 7/1987 |
| JP | 5186989 | 7/1993 |
| JP | 6305920 | 11/1994 |
| WO | 9115474 A1 | 10/1991 |
| WO | 9301716 A1 | 2/1993 |
| WO | 9403395 A1 | 2/1994 |
| WO | 9424869 A1 | 11/1994 |
| WO | 9614384 A1 | 5/1996 |
| WO | 9616148 A1 | 5/1996 |
| WO | 9803513 A1 | 1/1998 |
| WO | 9931215 A1 | 6/1999 |
| WO | 0045639 A1 | 8/2000 |
| WO | 2008088873 A1 | 7/2008 |
| WO | 2010050634 A1 | 5/2010 |

OTHER PUBLICATIONS

Tsunokawa, Youko, "A Versatile Method for Preparation of O-Alkylperoxycarbonic Acids: Epoxidation with Alkyloxycarbonlimidazoles and Hydrogen Peroxide", Tetradron Letters, vol. 23, No. 20, pp. 2113-2116. Jan. 1, 1982.

Klaas, Mark Rusch gen., Lipase-catalyzed preparation of peroxy acides and their use for epoxidation, pp. 311-319. Jun. 2, 1996.

Klaas, Mark Rusch gen., Lipase-catalyzed conversions of trimethylsilyl ethers: deprotection, acetylation, epoxidation and one-pot multi-step reactions, pp. 283-289. Feb. 26, 1999.

Klaas, Mark Rusch gen., et al, "Biocatalytic peroxy acid formation for disinfection", pp. 499-505. May 16, 2002.

Ogata, Y., et al, "The Formation of Peracids by the Perhydrolysis with Alkaline Hydrogen Peroxide", Tetrahedron, vol. 23, pp. 3327-3332. Dec. 13, 1996.

Muurinene, Esa, "Organosolv Pulping", dissertation presented to the faculty of technology, University of Oulu, Finland, 314 pages. Jun. 30, 2000.

Hatsuo, Maeda, "Assessment of Acyl Groups and Reaction Conditions in the Competition between Perhydrolysis and Hydrolysis of Acyl Resorufins for Developing an Indicator Reaction for Fluorometric Analysis of Hydrogen Peroxide", vol. 50, pp. 169-174. Feb. 28, 2002.

Leveneur, Sebastien, "Synthesis of peroxypropionic acid from propionic acid and hydrogen peroxide over heterogeneous catalysts", vol. 147, pp. 323-329. Nov. 20, 2008.

Effkemann, Stefan et al, "Peroxide analysis in laundry detergents using liquid chromatography", Analytica Chimica Acta, pp. 97-103. Jan. 2, 1998.

Dannacher, Josepf J., "Catalytic bleach: Most valuable applicatons for smart oxidation chemistry", Journal of Moleculor Catalysis, vol. 251, pp. 159-176. Mar. 20, 2006.

Carboni-Oerlemans, Chiara, "Hydrolase-catalysed synthesis of peroxycarboxylic acids: Biocatalytic promiscuity for practical applications", JRL of Biotech., vol. 126, pp. 140-151. Apr. 7, 2006.

\* cited by examiner

CONTINUOUS ON-LINE ADJUSTABLE DISINFECTANT/SANITIZER/BLEACH GENERATOR

CROSS-REFERENCE TO RELATED APPLICATIONS

This application is a continuation of U.S. Ser. No. 15/836,368 filed Dec. 8, 2017, which is a continuation application of U.S. Ser. No. 15/154,283 filed May 13, 2016 and entitled Continuous On-Line Adjustable Disinfectant/Sanitizer/Bleach Generator, which is a continuation application of U.S. Ser. No. 14/479,886 filed Sep. 8, 2014 and entitled Continuous On-Line Adjustable Disinfectant/Sanitizer/Bleach Generator, which is a divisional application of U.S. Ser. No. 13/330,981 filed Dec. 20, 2011 and entitled Continuous On-Line Adjustable Disinfectant/Sanitizer/Bleach Generator, which is a continuation-in-part of U.S. Ser. No. 61/427,951 filed Dec. 29, 2010, entitled Sugar Ester Peracid On-Site Generator and Formulator. The entire contents of these patent applications are hereby expressly incorporated herein by reference including, without limitation, the specification, claims, and abstract, as well as any figures, tables, or drawings thereof.

FIELD OF THE INVENTION

The invention relates to methods and apparatus for on-site generation of peracids, namely peroxycarboxylic acids and peroxycarboxylic acid forming compositions for use as oxidizing agents. In particular, an adjustable biocide formulator or generator system is designed for on-site generation of peroxycarboxylic acids and peroxycarboxylic acid forming compositions from sugar esters in a continuous manner. Methods of using the in situ generated peroxycarboxylic acids and peroxycarboxylic acid forming compositions are also disclosed.

BACKGROUND OF THE INVENTION

Peracids, also known as peroxyacids, are known for use as sanitizers, disinfectants, deodorizers, and bleaching agents, among other uses. Peroxycarboxylic acids in particular are known for use as antimicrobials and bleaching agents. Peracids such as peroxycarboxylic acid have known chemical disadvantages, namely, they are relatively instable in solution and decompose to ordinary oxyacids and oxygen.

Conventional peroxycarboxylic acid compositions are made through an acid catalyzed equilibrium reaction. Most often, the peroxycarboxylic acids are generated in a chemical plant, and then shipped to customers for on-site use. Due to the limited storage stability of peroxycarboxylic acids they are often packed in special containers and shipped under the strict Department of Transportation (DOT) guidelines. Certain improvements to peroxycarboxylic acid stability have proved advantageous for shipping purposes, as described in U.S. patent application Ser. No. 11/847,604, entitled "Shelf Stable, Reduced Corrosion, Ready to Use Peroxycarboxylic Acid Antimicrobial Compositions," the entire contents of which are hereby expressly incorporated herein by reference.

Most commercially available products in an equilibrium mixture contain excess hydrogen peroxide in the presence of stabilizers and acid catalysts, to stabilize and improve the composition's shelf life. Despite stability improvements, excess amounts of reagents (e.g., acids, oxidizing agents, and stabilizers) must be present in the compositions during shipping to prevent decomposition. Peroxycarboxylic acid instability, specifically limited storage stability, is described in detail in U.S. patent application Ser. No. 12/262,935, entitled "Enhanced Stability Peracid Compositions," the entire contents of which are hereby expressly incorporated herein by reference.

Accordingly, it is an objective of the claimed invention to develop methods and systems for on-site generation of peracids, including peroxycarboxylic acid generating compositions and peroxycarboxylic acids. In particular it is an objective of the invention to for on-site generation of biocide and antimicrobial agent comprising individual or mixed peracid chemistries.

A further object of the invention is to develop a system for generation of individual or mixed peracid chemistries according to user- or system-specific needs, such as those identified to address particular customer sanitation needs on-site for specific organisms.

A further object of the invention is to develop methods and systems for on-site generation of peracid chemistries to enhance efficacy performance, reduce transportation cost and hazards, reduce or eliminate wastes (eliminate use of excess ingredients to stabilize formulation) and enhance shelf-life of generated peracid chemistries.

A still further object of the invention is to develop a system for generation of peracid chemistries using sugar esters as backbone ingredients, which most preferably eliminates the use of builders and/or stabilizers.

Another object of the invention is to develop a system for peracid chemistry generation on-site where the acid is decoupled from peracid formulations to enable acids to be selected based upon desired performance criteria.

A further object of the invention is to develop a system for generation of peracid chemistries which enables a process information backbone.

BRIEF SUMMARY OF THE INVENTION

An advantage of the invention is a system for on-site generation of a biocide or antimicrobial agent. It is a particular advantage of the present invention that individual and/or mixed peracid chemistries, including peroxycarboxylic acid forming compositions or peroxycarboxylic acids are generated on-site according to particular needs of a user or system to provide desired performance against particular organisms. The system may be formulated into a number of designs, including for example, a mobile cart or generator that is particularly suitable for the on-site generation of peracid chemistries required in continuous preparations as opposed to batch formulations. In an embodiment, the present invention is an adjustable biocide formulator or generator system for on-site peroxycarboxylic acid forming composition generation including an apparatus with a continuous or in-line reaction vessel, a series of feed pumps for providing reagents for forming the peroxycarboxylic acid forming composition, and an outlet for dosing a peroxycarboxylic acid forming composition. In an embodiment the feed pumps are in fluid connection with the reaction vessel and supply reagents to produce the peroxycarboxylic acid forming composition and the reagents may include an ester of a polyhydric alcohol and a C1 to C18 carboxylic acid, a source of alkalinity, an oxidizing agent, and additional reagents according to the invention. In an embodiment the reaction vessel is in fluid connection with the outlet to dispense the peroxycarboxylic acid forming composition, which may be an individual or mixed peroxycarboxylic acid forming composition as selected by a user- or system-inputted selection.

In a further embodiment, the present invention is a method for on-site peroxycarboxylic acid forming composition or peroxycarboxylic acid generation and may include the steps of inputting a user- or system-controlled peroxycarboxylic acid forming composition or peroxycarboxylic acid formulation into a control software for an adjustable biocide formulator or generator system. In an embodiment the input formulation selects an individual or mixed peroxycarboxylic acid forming composition or peroxycarboxylic acid and corresponding volume or mass for on-site generation.

The methods of the invention further include the steps of diluting a source of alkalinity to a target concentration of less than about 20% by weight. The methods further include the steps of adding the ester(s) downstream (e.g. after the addition of the diluted alkalinity source solution).

In a further embodiment, the present invention is a method of cleaning using an on-site generated peroxycarboxylic acid forming composition and may include obtaining a user- or system-inputted peroxycarboxylic acid forming composition on-site using an adjustable biocide formulator or generator system and applying the peroxycarboxylic acid forming composition in an amount sufficient to sanitize, bleach or disinfect a surface in need thereof.

While multiple embodiments are disclosed, still other embodiments of the present invention will become apparent to those skilled in the art from the following detailed description, which shows and describes illustrative embodiments of the invention.

Accordingly, the drawings and detailed description are to be regarded as illustrative in nature and not restrictive.

Figure 1:
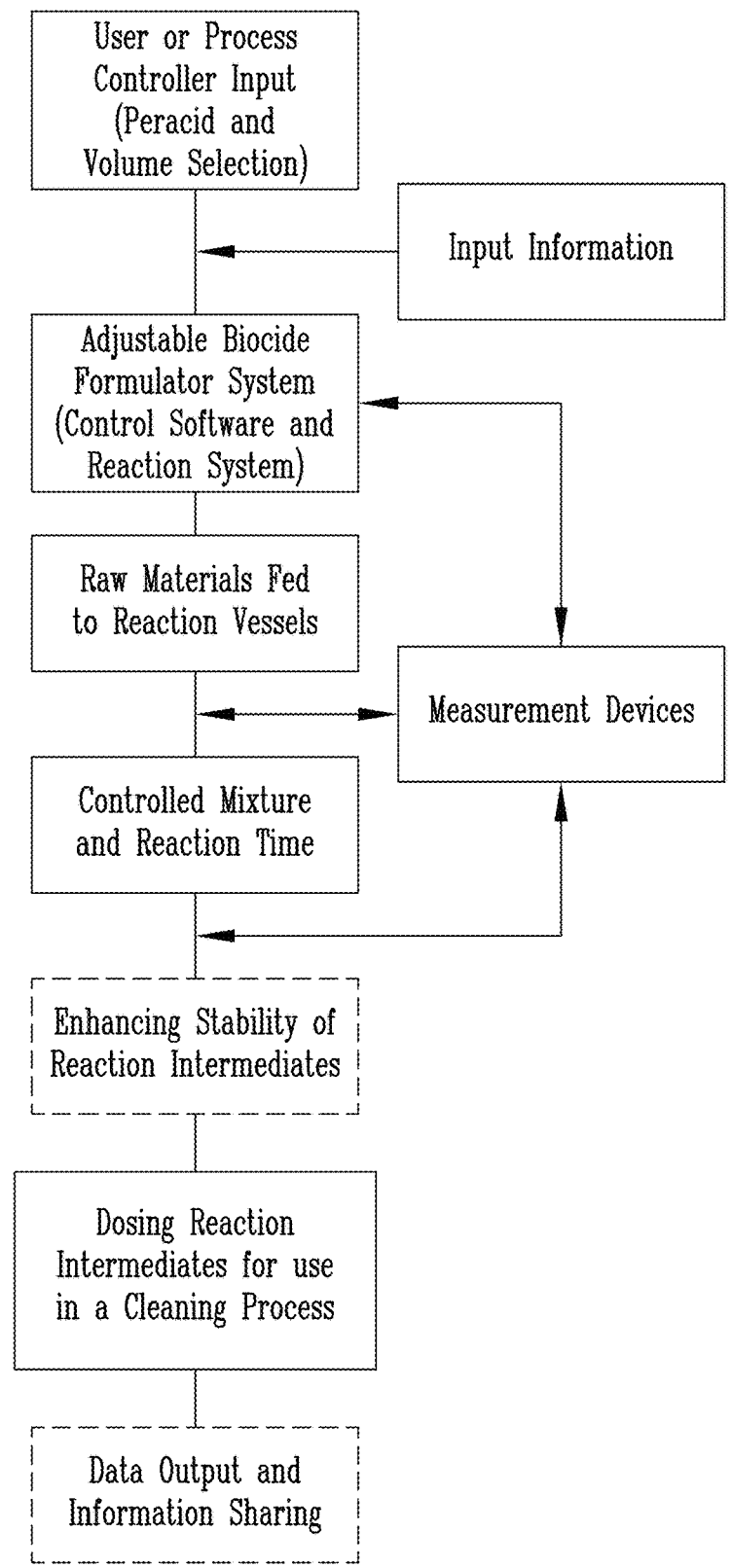
FIG. 1 shows a schematic diagram of a user or controller operated continuous adjustable biocide formulator apparatus according to the invention.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The present disclosure relates to adjustable biocide formulator or generator systems for on-site peracid generation, including for example peroxycarboxylic acid forming compositions or peroxycarboxylic acids, as well as methods of making and using such compositions. The compositions and systems for making the compositions disclosed herein have significant advantages over conventional systems and methods for making peroxycarboxylic acids or peroxycarboxylic acid forming compositions. For example, the systems allow on-site, user- or system-controlled formulation, eliminating the step of shipping hazardous peroxycarboxylic acid compositions to an end user. In addition, there are various advantages of the compositions, including having significantly lower levels of reactant residues compared to peroxycarboxylic acid compositions generated using equilibrium reactions, increased stability and ability to be generated in situ and/or on site.

The embodiments of this invention are not limited to particular methods and systems for on-site generation of sugar ester peracids for use as biocides, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, the phrase "air streams" includes food anti-spoilage air circulation systems. Air streams also include air streams typically encountered in hospital, surgical, infirmity, birthing, mortuary, and clinical diagnosis rooms.

The term "cleaning," as used herein, means to perform or aid in soil removal, bleaching, microbial population reduction, or combination thereof.

As used herein, the term "disinfectant" refers to an agent that kills all vegetative cells including most recognized pathogenic microorganisms, using the procedure described in A.O.A.C. Use Dilution Methods, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition and that is edible with or without further preparation. Food products include meat (e.g., red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the term "fouling" shall be understood to mean the undesirable presence of or any deposition of any organic or inorganic material in the applicable composition or chemistry.

As used herein, the term "free" or "substantially free" refers to a composition, mixture, or ingredient that does not contain a particular compound or to which a particular compound or a particular compound-containing compound has not been added. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning with a composition according to the present invention. As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the terms "mixed" or "mixture" when used relating to "peroxycarboxylic acid composition" or "peroxycarboxylic acids" refer to a composition or mixture including more than one peroxycarboxylic acid, such as a composition or mixture including peroxyacetic acid (POAA) and peroxyoctanoic acid (POOA).

As used herein, the terms "mixed," "mixture" or "more than one" when used relating to esters suitable for use in forming the compositions of the invention refer to a composition or mixture including more than one ester group undergoing a perhydrolysis reaction to form the peroxycarboxylic composition. The use of at least one ester of a polyhydric alcohol and a C1 to C18 carboxylic acid according to the invention includes the use of various forms of the ester, such as the mono, di, tri and/or mixtures thereof formations of the particular ester. Accordingly, examples of suitable forms of esters for use as "mixtures" or comprising "more than one" include, but are not limited to, glycerol monooctanoate, glycerol dioctanoate, glycerol trioctanoate, sorbitan monooctanoate, sorbitan dioctanoate, sorbitan trioctanoate, and mixtures and derivatives thereof. Further, as one skilled in the art shall ascertain based upon the description of the invention disclosed herein, the use of an ester source, such as glycerol octanoate, may further comprise the use of the mono, di and tri esters and/or mixtures thereof. According to various embodiments of the invention, the use of "an" ester, such as octanoic glyceride, may include the use of a "mixture" of esters wherein more than one formation of the ester is present, including for example the mono, di and tri formations and/or mixtures thereof.

As used herein, the phrases "objectionable odor," "offensive odor," or "malodor," refer to a sharp, pungent, or acrid odor or atmospheric environment from which a typical person withdraws if they are able to. Hedonic tone provides a measure of the degree to which an odor is pleasant or unpleasant. An "objectionable odor," "offensive odor," or "malodor" has an hedonic tone rating it as unpleasant as or more unpleasant than a solution of 5 wt-% acetic acid, propionic acid, butyric acid, or mixtures thereof.

As used herein, the terms "peracid" or "peroxy acid" refer to an acid having the hydrogen of the hydroxyl group replaced by a hydroxy group. Oxidizing peracids are referred to herein as peroxycarboxylic acids.

As used herein, the term "polyhydric alcohol" or "polyol," refers to an alcohol that has two or more hydroxyl groups. Polyhydric alcohols suitable for use in the compositions include, but are not limited to, sugars, sugar alcohols, and mixtures and derivatives thereof.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25+/−2° C., against several test organisms.

For the purpose of this patent application, successful microbial reduction is achieved when the microbial populations are reduced by at least about 50%, or by significantly more than is achieved by a wash with water. Larger reductions in microbial population provide greater levels of protection.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

As used herein the term "sugar" refers to carbohydrates including one, two, or more saccharose groups. Sugars are a group of organic compounds related by molecular structure that comprise simpler members of the general class of carbohydrates. Each sugar consists of a chain of 2 to 7 carbon atoms (usually 5 or 6). Sugars have the general formula $C_nH_{2n}O_n$, wherein n is between 2 and 7. One of the carbons carries aldehydic or ketonic oxygen which may be combined in acetal or ketal forms and the remaining carbon atoms usually bear hydrogen atoms and hydroxyl groups. In general, sugars are more or less sweet, water soluble, colorless, odorless, optically active substances which lose water, caramelize and char when heated. Exemplary sugars include, but are not limited to, glucose, sucrose, lactose and mixtures thereof.

As used herein, the term "sugar alcohol" refers to the hydrogenated form of a carbohydrate, wherein the carbonyl group of the carbohydrate has been reduced to a primary or secondary hydroxyl group. Sugar alcohols have the general formula $CH_2OH(CHOH)_nCH_2OH$, wherein n is from 2 to 5. Exemplary sugar alcohols include, but are not limited to, glycol, ethylene glycol, propylene glycol, glycerol, erythritol, pentaerythritol, threitol, arabitol, xylitol, ribitol, mannitol, sorbitol, sorbitan, dulcitol, iditol, inositol, isomalt, maltitol, lactitol, polyglycitol, 1,4-cyclohexane diol, and mixtures and derivatives thereof. In some embodiments, the sugar alcohol is selected from ethylene glycol, propylene glycol, glycerol, polyglycerol, sorbitol, sorbitan, and mixtures and derivatives thereof.

As used herein, the term "ware" refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. Ware also refers to items made of plastic. Types of plastics that can be cleaned with the compositions according to the invention include but are not limited to, those that include polycarbonate polymers (PC), acrilonitrile-butadiene-styrene polymers (ABS), and polysulfone polymers (PS). Another exemplary plastic that can be cleaned using the compounds and compositions of the invention include polyethylene terephthalate (PET).

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and hand-wash dip-pans, third-sink rinse waters, and the like. Waters also include domestic and recreational waters such as pools, spas, recreational flumes and water slides, fountains, and the like.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

Embodiments of the Invention

According to an embodiment of the invention methods and apparatus for on-site generation of peracid chemistries for use as cleaning agents, including for example, antimicrobial applications, bleaching applications, and other cleaning and anti-scaling applications. The methods and apparatus according to the invention are capable of on-site generation of both individual or mixed peracid chemistries formulated according to user-specifications. In particular, the methods and apparatus according to the invention provide for continuous generation of the particular chemistries selected by a user. In addition, the methods and apparatus provide for the generation of large volumes of the user selected chemistries. Beneficially, the methods and apparatus according to the invention may be used at flow rates varying from mL per minute to liters per minute. For example, various embodiments of the invention (including as set forth in the Examples) use flow rates of approximately 25 mL/minute and can be scaled up to rates as great as liters/minute.

The invention overcomes the shortfalls of commercially-available peracids by providing user-specific formulations with enhanced performance efficacy through continuous, non-equilibrium methods of making. In addition, the methods and apparatus use sugar esters as backbone ingredients to generate on-site peracid chemistries, beneficially reducing the costs and hazards associated with transporting active chemistries, providing active chemistries with increased shelf-lives and reduction of waste of active chemistries as a result of on-site user-identified peracid production according to the invention. In particular, there is the elimination of significant waste of chemistry streams through the non-equilibrium (as opposed to acid catalyzed equilibrium reactions) methods of making, further reducing the need for hazardous shipping conditions of conventional peracid chemistries.

While an understanding of the mechanism is not necessary to practice the present invention and while the present invention is not limited to any particular mechanism of action, it is contemplated that, in some embodiments the benefits afforded according to the invention result from the production of a non-equilibrium chemistry using the methods and apparatus of the present invention. Beneficially, the reacted peracids according to the invention are obtained in greater amounts than in equilibrium chemistry wherein greater amounts of unreacted hydrogen peroxide and other reagents would be present. According to the present invention, an aqueous solution of the peroxycarboxylic acid(s) produced contains a relatively higher concentration of peroxycarboxylic acid(s) compared to unreacted hydrogen peroxide component. This is significantly advantageous for the anti-microbial and other cleaning applications disclosed herein as desirable according to the embodiments of the invention.

Rather than providing a peracid composition in an equilibrium mixture, in situ generation of the peracid composition allows the peracids to be produced stoichiometrically through selecting the composition of the starting materials. The in situ systems according to the invention therefore generate higher concentrations of the peroxycarboxylic acid(s) than are available in equilibrium systems. In particular, the in situ systems according to the invention therefore generate higher concentrations of the peroxycarboxylic acid(s) and lower concentrations of hydrogen peroxide (e.g. unreacted reagents) than are available in equilibrium systems. In addition, the methods of the present invention generate peroxycarboxylic acid(s) under alkaline conditions and thereafter adjust to acidic conditions to stabilize the peroxycarboxylic acid(s) and ensure the peroxycarboxylic acid(s) compositions do not disassociate.

Continuous System for Making On-Site Peracid Compositions

In some aspects, the present invention relates to an adjustable biocide formulator or generator (ABF) system for the continuous, on-site generation of peracid chemistries. As used herein, the terms ABF, ABF system/apparatus/generator and the like refer equally to the various embodiments of the invention disclosing the continuous adjustable biocide formulator, apparatus and/or system disclosed herein according to the various embodiments. The ABF system produces peroxycarboxylic acid forming compositions according to the disclosure presented herein. Peroxycarboxylic acid forming compositions refer to the generation of peroxycarboxylic acids in situ, in a non-equilibrium reaction. In particular embodiments of the invention, the adjustable biocide formulator or generator system produce the anion capable of forming peroxycarboxylic acid upon acidification. According to additional aspects of the invention, the ABF system may produce peroxycarboxylic acids.

Beneficially, the ABF system according to the present invention provides an apparatus designed to produce peracid chemistry in a continuous manner, rather than in batch modes. In addition, the continuous manner of peracid generation provides for the supply of chemistries in large quantities and production rates. According to the invention, there are numerous applications for the apparatus and methods of the present invention having increased chemical use demands requiring modifications to enable continuous chemistry generation.

The ABF systems and methods according to the invention obviate the need for larger-sized reactors and/or increasing the number of reactors and requiring staggering-start modes as previously required in the first generation ABF systems disclosed in U.S. patent application Ser. No. 61/427,951, entitled Sugar Ester Peracid On-Site Generator and Formulator. Further, the present invention significantly simplifies the ABF apparatus through the elimination of various apparatus components as a result of apparatus design (e.g. valves, mixers, vessels, etc. and combinations of the same). The ability to simplify the ABF system and eliminate numerous components results from the use of the pump system and the modified reaction vessel (e.g. reaction manifold).

In some aspects, the system for on-site generation of peroxycarboxylic acid forming compositions may comprise, consist of and/or consist essentially of an apparatus including at least one reaction vessel, a series of feed pumps and an outlet for dosing the generated chemistry from the reaction vessel. According to embodiments of the invention, the reaction vessel, as used herein, describes a variable length, tubing diameter, tubing material and flow pattern of a reaction tubing or manifold, as one skilled in the art will understand from the disclosure of the present invention. The terms "reaction vessel," "reaction manifold" and the like shall be understood to refer to the location of the perhydrolysis reaction according to the invention. Preferably, the reaction manifold is embodied as a flow through reactor for the perhydrolysis reaction according to the invention.

In some aspects, the reaction manifold, series of feed pumps and the outlet are in fluid connection to provide the raw starting materials (e.g. reaction reagents) used to generate the peroxycarboxylic acid forming composition in the reaction manifold. In some aspects, the system may also include one or more reservoirs in fluid connection with the reaction manifold to allow further mixing and/or storage of the peroxycarboxylic acid forming compositions. In some aspects, the system may optionally comprise at least one measurement device.

In some aspects, the delivery rates of the reagents are balanced against the chemical demand of the application. In particular, the reaction manifold is sized by selecting the appropriate reactor length and inner diameter (volume) to achieve proper reaction time for the specified chemistry.

In some aspects of the invention the ABF system does not include any systems or components for mixing the reagents in the reaction manifold (e.g. mixers, impellers or the like). Beneficially, the design of the reaction manifold obviates the need for such components as a result of the length and/or shape of the reaction manifold. Instead, the pumping of raw starting materials through the reaction manifold is sufficient for mixing of the components for the perhydrolysis reaction to take place. Alternatively, additional modifications to the reaction manifold can be made to further assist in mixing of the reagents, such as using baffles, continuous stirred-tank reactors (CSTR) or other means for interrupting the flow of liquid (e.g. disrupting the laminar flow through the reaction manifold). As one skilled in the art of chemistry reaction kinetics will ascertain, the use of variable pumps and injection manifolds for providing the reagents can be varied to adjust the rate and amount of reagents added to a particular system.

In some aspects an injection manifold is provided to source individual reagents for the chemistry generation according to the invention. In alternative aspects of the invention, an injection manifold may have fewer inputs into the system, as reagents may be combined into one or more premixes. One skilled in the art will ascertain that the variability in the construction and design of the injection manifold for providing the reagents to the reaction manifold of the system. For example, one or more injection manifolds may be incorporated into a system to provide reagents at different times and/or locations of the reaction manifold (e.g. to time the addition of the sugar esters for the production of mixed peracid chemistries). These and other modifications of the system are within the scope of the invention and will be appreciated by a skilled artisan.

In some aspects of the invention, the reaction manifold meets the hydraulic requirements of the peracid reaction kinetics. Although not intending to be limited by a particular theory of the invention, the kinetics of the perhydrolysis reaction according to the invention are pH, concentration and/or temperature dependent, and the reaction can reach the maximum yield in the order of minutes. The reaction manifold and components of the ABF system may be designed in a variety of ways, including for example shape, size, temperature, fluid dynamics (e.g. pumping or other means to modify the hydraulics of the system) and material.

In additional aspects of the invention, the pumps providing the reagents into an injection manifold may be pressurized. In a preferred embodiment, the pumps create a pressure differential within the feed pumps and/or reaction manifolds. The systems according to the invention may further include a pressure gauge to measure such pressure differential and provide system feedback for adjusting the pressure created by the pumps. For purposes of improving the pressure within a system, the apparatus may further include the use of an injection quill to ensure the movement of reagents through the feed pumps and/or reaction manifold with the highest velocity.

In some aspects of the invention, the system for on-site generation of peroxycarboxylic acid forming compositions may include at least one measurement device or a plurality of measurement devices. Such measurement devices are those suitable to measure one or more reaction kinetics or system operations for the generation of peroxycarboxylic acid forming compositions, including for example devices to measure fluorescence, weight, flow (e.g. flow meters or switches), capacitive level, pH, oxidation reduction potential, pressure, temperature and combinations thereof. Such measurement devices may measure the system's feed pumps, reaction manifold, reservoir, outlets, etc.

Examples of additional suitable measurement devices include capacitive level sensors, out of product alarms, POA/peroxide monitors, oxychecks, IR/UV/VIS spectroscopy and pressure switches. Still further examples of suitable measurement devices are disclosed herein, in addition various embodiments of those disclosed in U.S. patent application Ser. No. 12/108,202, and U.S. Pat. No. 7,547,421, both entitled Apparatus and Method for Making Peroxycarboxylic Acid, which are herein incorporated by reference in their entirety.

In some embodiments of the invention, the system provides an acid source for the acidification step to take place in the ABF system. The acid source may be an acid or an aqueous acid solution. As a result the peroxycarboxylic acid forming composition is acidified to peroxycarboxylic acid within the system. In an embodiment of the invention, the system may include a feed pump to provide an acid or acidic aqueous solution in fluid communication with the reaction manifold or a reservoir. The addition of the acid or acidic aqueous solution may dilute the peroxycarboxylic acid forming composition to form a peroxycarboxylic acid having a pH of about 1.0 to about 8.0. As a result, a stabilized formulation is generated by the system. According to certain embodiments, the addition of the acid or acidic aqueous solution produces peracid formulations with increased stability. However, as one skilled in the art will appreciate, some reaction intermediates are stable for longer periods of time and do not need to be quenched with acid immediately. For example, some reaction intermediates are stable for at least 24 hours and can be pumped to a sump reservoir for dosing into a cleaning process or dosed directly from the reaction manifold. Other peroxycarboxylic acid forming compositions are less stable and the perhydrolysis reaction requires quenching with the acid or acidic aqueous solution to lower the pH and stabilize more promptly.

According to alternative embodiments of the invention, the ABF system generates peroxycarboxylic acid forming compositions which are acidified outside of the system (i.e., post generator within a customer's process). For example, post-generator acidification may include a clean in place (CIP) process where the peroxycarboxylic acid forming composition (anion solution) is pumped to a temporary holding tank for use in a CIP system, or pumped directly to a CIP system where the acid is added either in a pipe or the CIP vessel itself. A further example of post-generator acidification may include a healthcare application or certain laundry applications where the acid is added to provide a peroxycarboxylic acid (with an acid pH) to provide bleaching and/or sanitizing benefits of the peracid.

According to additional embodiments of the invention, there are various applications for the compositions of the invention where acidification is not required and/or desired as the use of the peroxycarboxylic acid forming composition (anion solution) is preferred. For example, in a laundry application the acid is not be added in order to benefit from the alkaline pH of the anion for bleaching purposes. The alkaline pH for bleaching is obtained from the anion species, as a result the peroxycarboxylic acid forming composition is not quenched with acid.

In some aspects of the invention, the system may include a variety of safety mechanisms. Exemplary on-site safety feedback mechanisms for a system are disclosed in further detail in U.S. Patent Publication No. 2009/0208365, which is hereby expressly incorporated by reference including, without limitation, the specification, claims, and abstract, as well as any figures, tables, or drawings thereof. Various safety mechanisms can measure pressure, temperature, difference in pressure, difference in temperature, or a combination thereof and provide a perceptible signal if one or more of these increases above a predetermined level. The level of pressure, temperature, difference in pressure, difference in temperature, or a combination thereof at which safety system provides a perceptible signal can be selected to allow intervention to avoid undesirable or unsafe conditions.

In another aspect of the invention, the system may include a cooling system on the reaction manifold. A cool system may be in combination with a safety mechanism and/or a measurement device of the system. It may be desirable to have the reaction manifold and/or other components of the system under temperature controls. As one skilled in the art will appreciate, exothermic reactions may degrade the reagents according to the generation of the peracid compositions of the invention. In addition, there are various safety considerations for a system to avoid increases in temperature, for example system temperatures in excess of 110° C. In addition, according to an embodiment of the invention, the system has at least one mechanism to cool a reaction vessel and/or other components of the system. Such mechanisms may include, for example, a quenching mode, increased surface area, cooling jacket, venting systems, cold finger, and the like.

In some aspects, the system for making on-site peracid chemistry formulations does not require the use and/or incorporation of any microprocessor control of the system. This is a significant benefit of the system design as it reduces the cost of the ABF system. As opposed to including a controller and/or software platform, the system is configured to prepare a single specific formulation in which the reagent delivery pumps are calibrated to meet the formulation specifications. The pump rate is selected to balance peracid generation against product use.

In alternative aspects, the system for making on-site peracid chemistry formulations may further comprises an optional controller or software platform to prepare a multitude of formulations. The software platform provides a user or system to select a generation mode for a desired peracid formulation for on-site generation. As a result, use of the system for onsite peracid chemistry generation provides significant user flexibility to generate chemistries for particular user-identified purposes. For example, the controller or control software for operation of the system may permit a user or system to select both the peracid formulation, the desired volume of the formulation and/or rate of formulation for on-site generation. In a further aspect, the control software may determine the timing, sequencing and/or selection of feeding raw materials (e.g. reagents) into the system, mixing time and total reaction time required for production of the user- or system-selected peracid formulation within the reaction manifold. The selection of the chemistry formulation and generation rate adjusts the reagent feed pumps accordingly, in addition to the length of the reaction manifold (e.g. tubing and therefore the reaction time for the perhydrolysis reaction) through which the reagents flow for the reaction to proceed to desired completion.

According to the invention, the controller may further include a mechanism for manually starting/stopping any of the same functions, including for example a manual switch panel for the same. In addition to manual controls, such as a manual switch panel, the controller preferably has buttons or other means for selecting particular embodiments according to option displayed by the control software platform. An embodiment of the controller may further include a display screen to assist a user in selecting a generation mode for a desired peracid formulation and any other options for user selection as one skilled in the art will ascertain based upon the description of the invention. Concomitant with the control software are user-friendly instructions for use displayed on the display screen (or the like).

In an aspect of the invention, the control software utilizes a control software algorithm to maximize on-site active chemistry yield and provide safe operating conditions for the reactor manifold of the system. The control software permits user-identified chemistry production to be run in the reaction manifold and to properly sequence reactions to obtain active chemistries.

Examples of suitable controllers are disclosed herein, in addition various embodiments of those disclosed in U.S. patent application Ser. No. 12/108,202, and U.S. Pat. No. 7,547,421, both entitled Apparatus and Method for Making Peroxycarboxylic Acid, which are herein incorporated by reference in their entirety.

In another aspect of the invention, the system may include a data output means for sharing information related to the peroxycarboxylic acid forming compositions and/or peroxycarboxylic acid formulations generated according to the system. For example, an information backbone may be used to both collect and disseminate data from the process of generating the peracid formulations including, for example, composition consumption, dispensing or usage, and additional formulation production-related data. Such data may be generated in real-time and/or provided in a historical log of operational data detectable or storable by a user or system. In an embodiment of the invention a user or system is able to monitor usage and performance, including for example, chemistry dispensing, managing chemistry distribution to various point-of-use applications, communication with system operators to control and monitor chemistry dispensing, allocation and/or formulation and the like. According to an additional embodiment of the invention, a user or system is able to control systems, including program systems, remotely.

According to an aspect of the invention, any system operations suitable for use with the invention may be controlled and/or monitored from a remote location. Remote system operations control and/or monitoring may further include the system updates and/or upgrades. According to an aspect of the invention updates and/or upgrades to system operations may be downloaded remotely. These and other embodiments of data output means, information sharing, remote system operations and the like, which may be adapted for use with the present invention, are further described, for example, in U.S. Pat. Nos. 7,292,917, 6,895, 307, 6,697,706 and 6,377,868 and U.S. Patent Publication Nos. 2005/0102059, 2005/0065644, 2004/0088076, 2003/0195657 and 2003/0195656, which are hereby expressly incorporated by reference including, without limitation, the specification, claims, and abstract, as well as any figures, tables, or drawings thereof.

In another aspect of the invention, the data output for sharing information related to the compositions according to the system may coordinate multiple systems on at a single site. According to this embodiment of the invention, information sharing between the multiple systems may take places place using any communications network capable of coupling one or more systems according to the present invention, including for example, using a server computer and a database.

Exemplary Systems Depicted by Figures

According to an embodiment of the invention, as shown in FIG. 1, a user or process controller input, such as a CIP or tunnel washer process controller, selects a peracid formulation desired for on-site generation for a specific cleaning application. The user or process controller input selects both the chemistry formulation and how much is needed (i.e., gallons use solution) and such input information is loaded into the ABF system. Control software, including a software algorithm, may be used to calculate the timing and sequencing for dosing the raw materials needed for the particular peracid chemistry generation. Raw materials are fed into the reaction vessels of the system under controlled mixture and reaction times. The system may employ a variety of measurement devices providing feedback to the system. Optionally, for generation of a peroxycarboxylic acid formulation (as opposed to the anion peroxycarboxylic acid forming compositions), the stability of the reaction intermediates may be enhanced by adding an acid or aqueous acidic solution. The system provides the user or process controller selected peracid formulation for use in a cleaning process, including without limitation, antimicrobial, bleaching, sanitizing and/or antiscaling applications. In addition, various data output and information sharing methods may optionally be employed according to the methods and systems of the invention.

Figure 2:
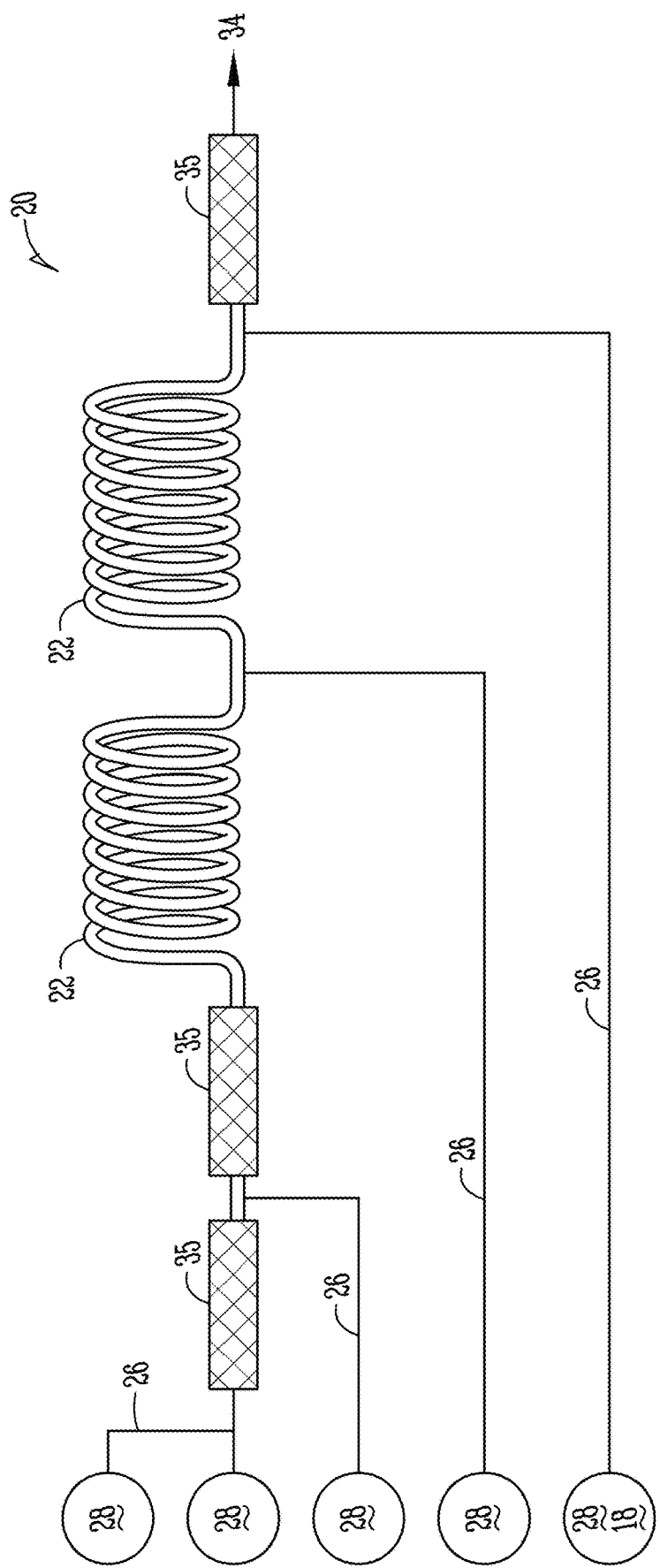
FIG. 2 shows a diagram of an embodiment of an adjustable biocide formulator apparatus according to the invention wherein a plurality of pumps dosing raw starting materials (e.g. reagents) are provided to a reaction vessel (e.g. manifold).
Figure 3:
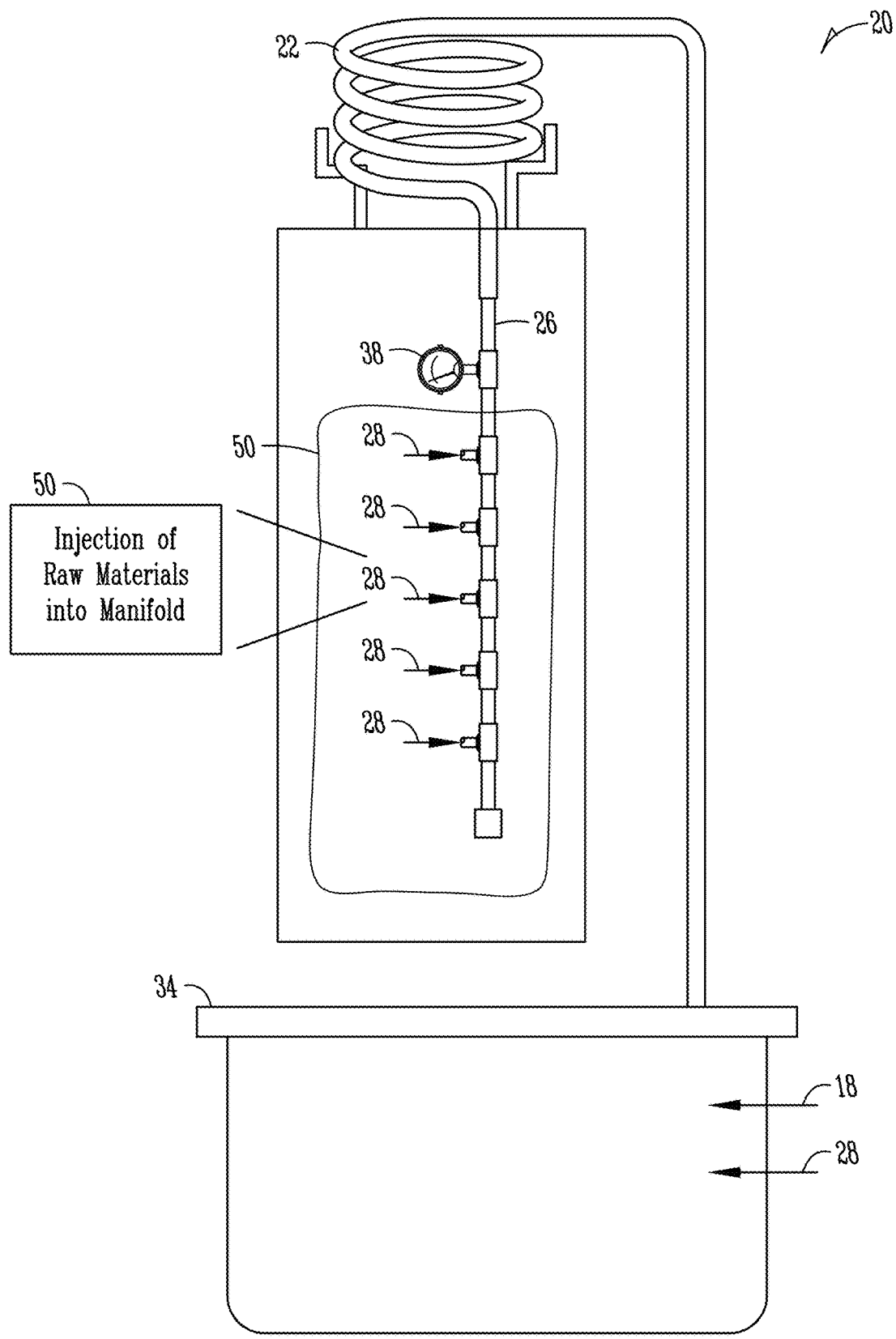
FIG. 3 shows a diagram of an embodiment of the adjustable biocide formulator apparatus according to the invention.

Embodiments of the system 20 are further shown in FIGS. 2 and 3. The apparatus of the ABF system 20 may comprise one or more reaction manifolds 22 for the generation of the user or process controller selected peracid formulations. FIG. 2 shows an embodiment of a reaction manifold 22 for the continuous generation of peracid chemistry. As depicted in a diagram form, one or more peracids can be generated using a reaction manifold(s) 22 as opposed to reaction vessels 22 described in related application U.S. Ser. No. 13/330,915, filed simultaneously herewith and incorporated by reference. To produce a mixed peracid chemistry in a reaction manifold 22 system 20, peracids may be produced through the timed addition of more than one sugar ester 24 (e.g. a raw starting material 28) according to the particular hydrolysis reactions to ensure that the reactions are completed at the same time. Sequencing of raw material 28 feeds is critical to producing the correct formulation of peracid-based chemistry. For example, peroxyoctanoic acid (POOA) and peroxyacetic acid (POAA) can be generated through the addition of the sugar esters sorbitol octanoate and triacetin 28 to a reaction manifold 22, respectively, despite the fact the hydrolysis reactions occur at different rates. The POAA reaction takes place quickly and the POOA reaction takes place slower. Timing the addition of the sugar ester in excess peroxide at alkaline pH and accurately dosing the amount of sugar ester can be controlled to generate the desired peracid chemistry formulation. As a result of the ABF system 20 timing the addition of the raw starting materials 28 (e.g. sugar esters 24) such that the sugar esters 24 are reacted in the desired location of the reaction manifold 22 for predetermined reaction times and then dispensed from the reaction vessel 22 to a sump reservoir 34 (may also be referred to as a dilution tank 34) to a cleaning process 38.

In addition to the preferred embodiment of using timed addition of raw starting materials 28 for measuring the extent of hydrolysis reactions according to the invention, alternative embodiments include reactions based upon volume, weight and/or additional methods to produce a preferred for individual peracid chemistry. The ABF system 20 according to the invention may use various methods to measure the extent of a reaction, including for example, temperature rise, oxidation reduction potential and/or pH. The desired peracid systems selected by a user and/or system (including volume of the peracid system) may impact the hydrolysis reactions. However, it is an advantage of the present invention that the ABF system accommodates for such variations and changes.

As shown in FIG. 2 the raw starting materials 28 (including sugar esters 24) are added to a system via feed pumps 26 into the reaction manifold 22. The systems may optionally include mixers or means for mixing the raw starting materials 28 as they are added into the reaction manifold for dilution, perhydrolysis, etc. The proper sequencing and timing ensures that both perhydrolysis reactions generate reaction intermediates that are completed at the same time. For any of the exemplary and non-limiting systems depicted in the figures, the apparatus of the ABF system 20 may include a system of feed pumps 26 fluidly connecting the sugar esters 24 and other raw starting materials 28 to the reaction vessels 22 of the system. The raw starting materials 28 may include any raw material source, including for example sugar esters 24, oxidizing agent, alkalinity source, water, catalysts, water, air, etc. According to the embodiment of FIG. 2, the raw starting materials 28 are depicted as originating from separate containers or sources. However, as the figures depict non-limiting examples of the system, the raw starting materials may be combined into various premix formulations to reduce the number of raw starting materials individually combined into a system, although preferably the reaction catalyst and precursor sugar ester are provided from separate feed pumps 26.

Feed pumps 26 may feed raw starting materials 28 by various suitable mechanisms known to those skilled in the art. According to an embodiment, feed pumps 26 may feed by tick on a flow meter, wherein the flow meter is calibrated in advance. According to an additional aspect of the invention, a positive displacement pump can be used to count pump strokes for a diaphragm pump or revolutions for a peristaltic pump. Preferably, feed pumps 26 are calibrated prior to use of the system. Raw materials 28 are fed to the reaction manifold 22 sequentially or in parallel, as some raw materials 28 may be fed to the reaction vessel(s) 22 at the same time. Raw materials 28 according to the invention include for example, sugar esters 24, oxidizing agent, alkalinity sources, and water. The raw materials 28 are mixed in reaction vessel(s) 22 for a sufficient period of time for perhydrolysis reaction to take place.

In addition, the ABF system 20 may further comprise an acid or aqueous acidic solution source 18 in fluid communication with the reaction manifold 22, reservoir 34 and/or system outlets 36. According to some aspects of the invention, the system 20 measures the extent of the perhydrolysis reaction to determine when to quench the reaction with the acid or aqueous acidic solution source 18 in order to generate a peroxycarboxylic acid formulation. The addition of the acidulant according to the invention increases the solubility of the peroxycarboxylic acid(s). For example, according to the invention, the peroxycarboxylic acid(s) solution may be transported safely without loss of the peracid content. The peroxycarboxylic acid(s) solution may further be diluted to a final use concentration. As one of skill in the art shall ascertain, additional acid may be required for the pH to be in accordance with the certified levels.

According to the invention, certain measurement devices may be employed to determine the extent of the perhydrolysis reaction for dosing of the acid or aqueous acidic solution source 18. Measurement devices can include, for example, time, temperature, oxidation reduction potential, pH, etc. FIG. 3 shows a further depiction of an embodiment of the invention. An injection manifold 50 using a pneumatic supply is depicted wherein raw starting materials 28 (according to any of the embodiments described herein, including for example premix formulations) are added to a system 20 via feed pumps 26 into the reaction manifold 22. The systems may optionally include mixers or means for mixing the raw starting materials 28 as they are added into the reaction manifold 22. Alternatively, the continuous flushing of the reaction manifold 22 with the raw starting materials 28 according to the invention may provide suitable mixing for the perhydrolysis reaction to occur. As depicted in FIG. 3, a pressure gauge and/or source of compressed air 38 may be incorporated into the system. (Include description of significance).

The system 20 of FIG. 3 depicts a non-limiting embodiment of the reaction manifold 22 according to the invention. In particular, a vertically spiraled, helical track is implemented as the reaction manifold. Beneficially, this embodiment assists in removing gas that may be generated from the system (and may optionally further include the use of permeable membranes to further assist in the elimination of gas from the system). The system 20 further depicts the flow of raw starting materials 28 added via an injection manifold 50 through the reaction manifold 22 and provided to a sump reservoir or dilution tank 34. The peracid chemistry may be diluted with a water source 28 and/or acidified with an acid source 18 within the sump reservoir or dilution tank 34 and is then stored until transfer for use in a cleaning process 38.

Figure 4A:
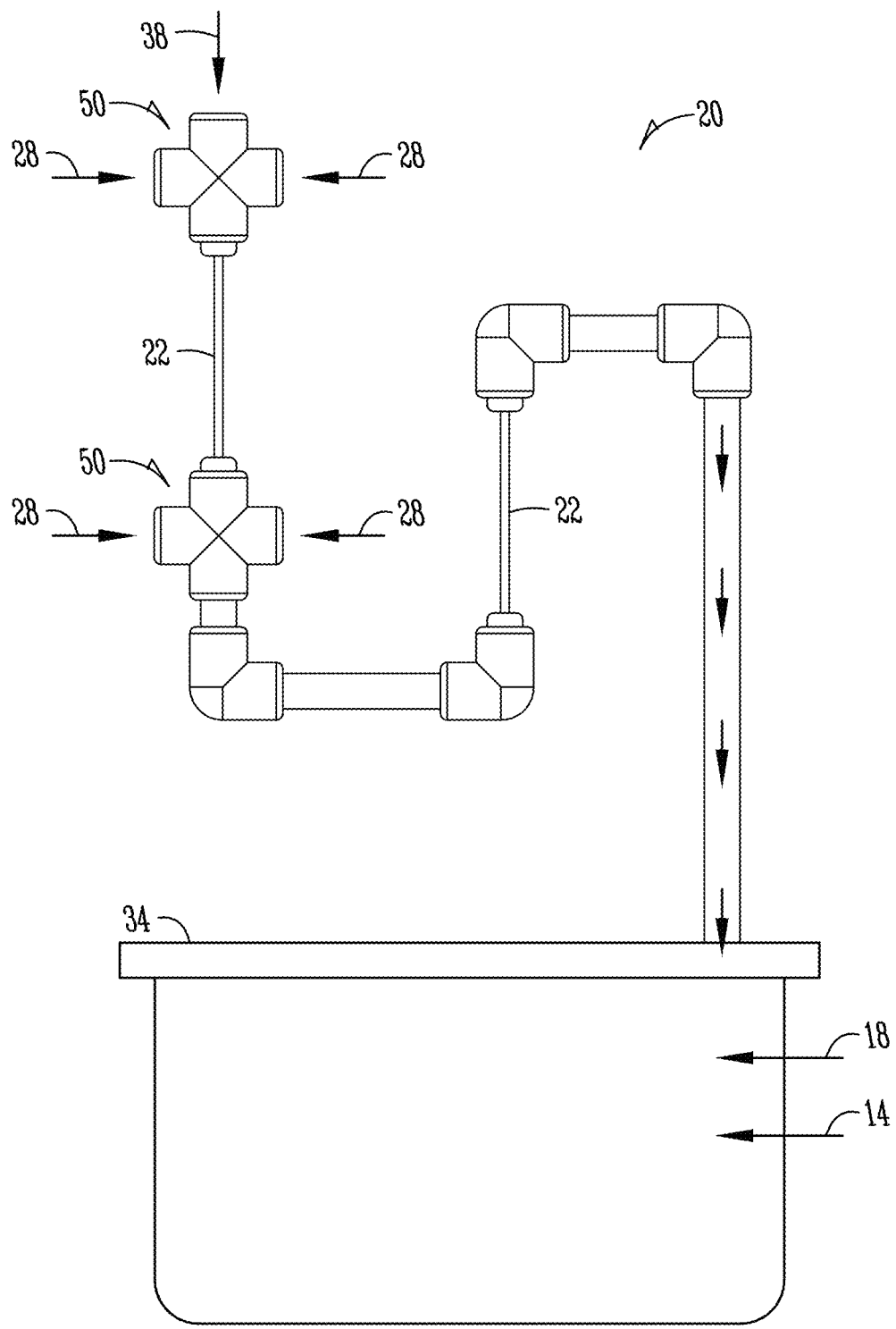
FIGS. 4A-B shows a diagram of an additional embodiment of the adjustable biocide formulator apparatus according to an embodiment of the invention.
Figure 4B:
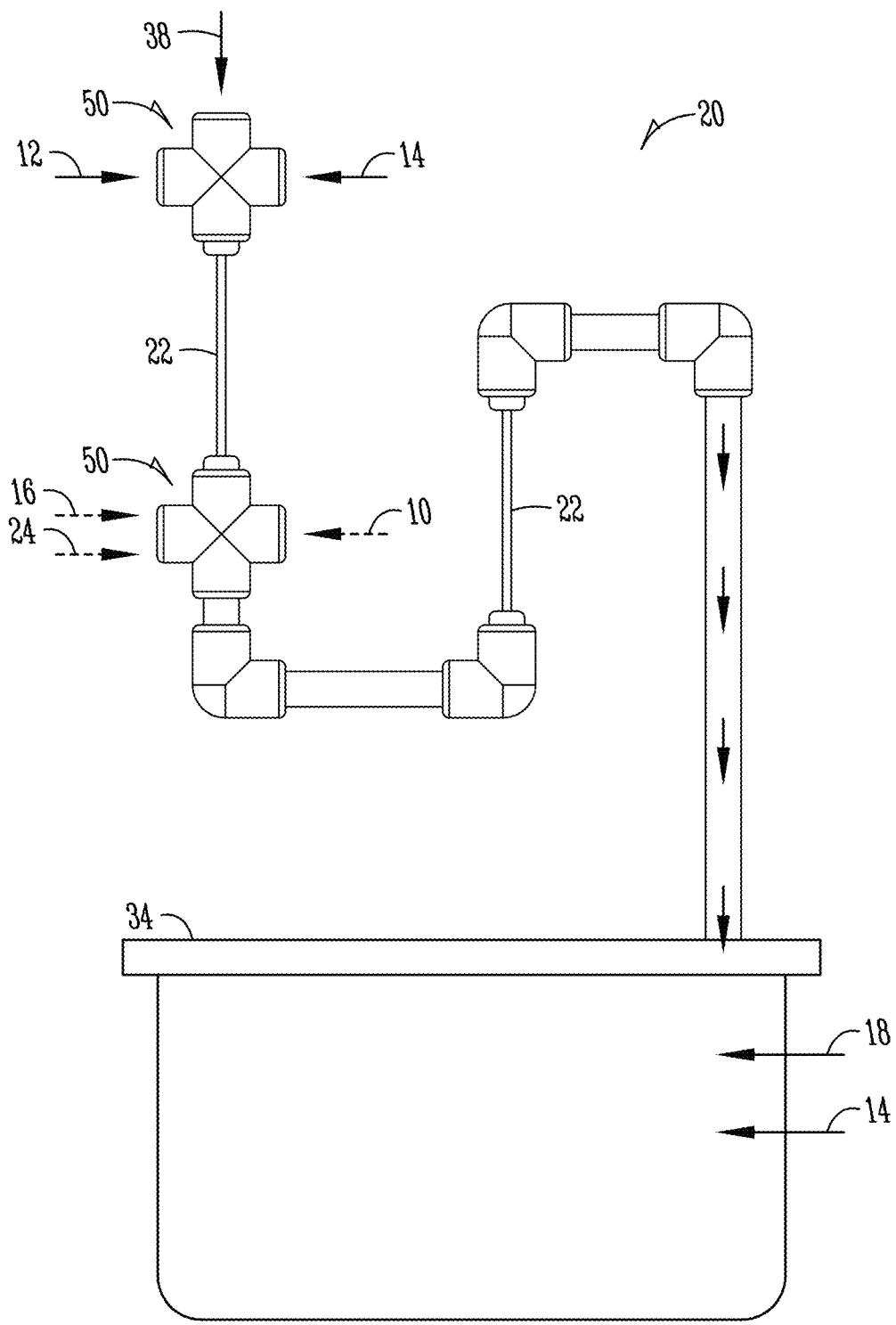

FIG. 4A shows a further embodiment of the invention wherein the ABF system 20 uses various injection manifolds 50 for the timed addition of raw starting materials 28. According to the particular depicted embodiment, a source of compressed air 38 is used in the first injection manifold 50 to aid in the mixing of the chemistry within the reaction manifold 22. Thereafter a second injection manifold 50 provides additional raw starting materials 28 prior to mixing the chemistry within a further portion of the reaction manifold 22. Thereafter the chemistry is provided FIG. 4B shows a further embodiment wherein particular raw starting materials are selected for the timely addition to the system 20 to promote the efficiency of the chemistry production. In particular, NaOH 12 and water 14 are provided at a first injection manifold 50 to the reaction manifold 22 of the system. Thereafter, the diluted caustic is combined with an ester premix 16 (or its individual components shown as an ester 24 and a peroxide source 10) and continues to move through the reaction manifold 20 for the perhydrolysis reaction according to the invention. The chemistry is they provided to a sump reservoir or dilution tank 34 where the chemistry may be diluted with water 14 and/or acidified with an acid source 18, where it is then stored until transfer for use in a cleaning process 38.

Figure 5:
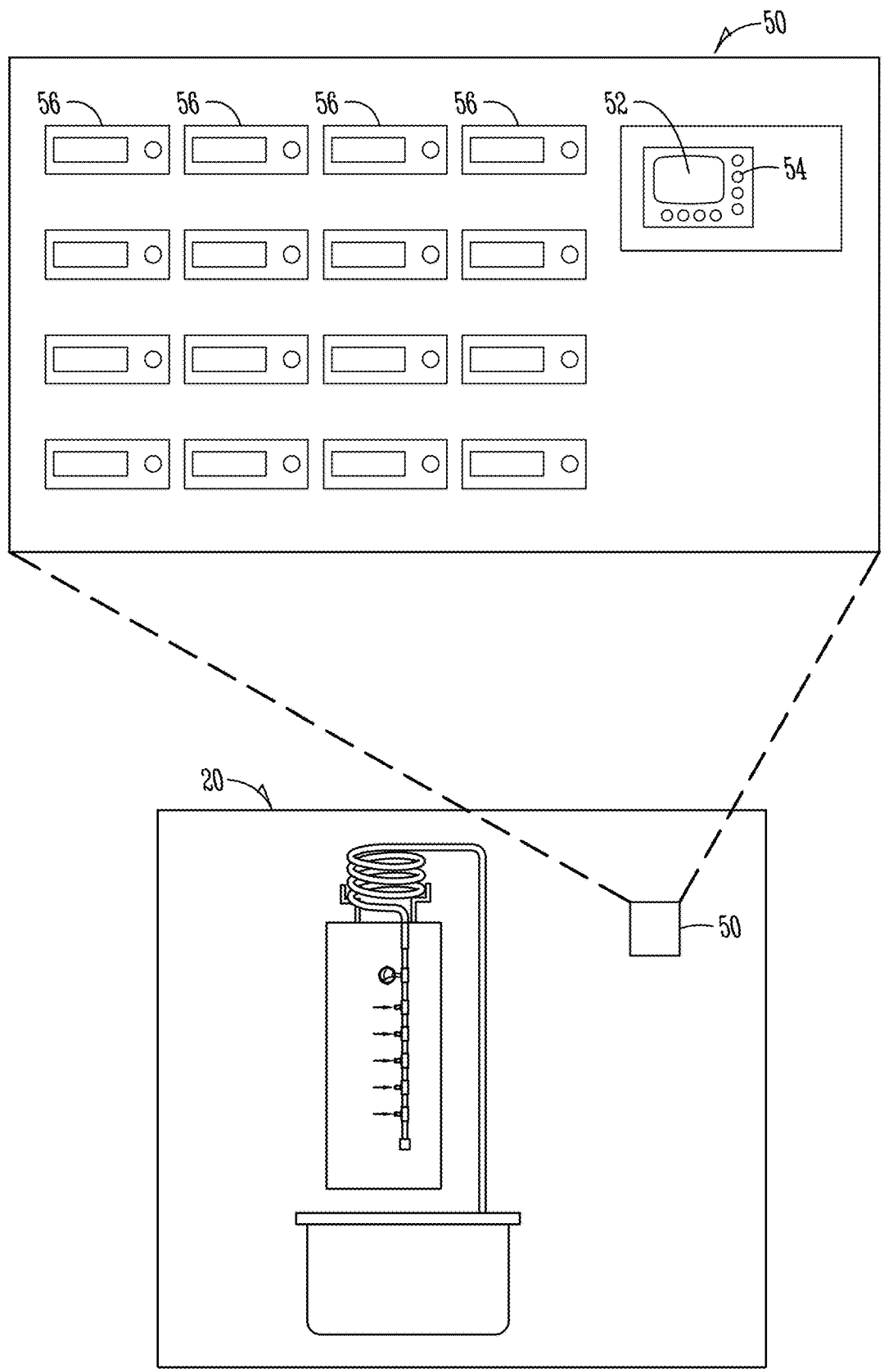
FIG. 5 shows a diagram of an embodiment of an adjustable biocide formulator apparatus according to the invention wherein a controller is included as a feature of the apparatus.

FIG. 5 shows an expanded view of a controller 50 according to an embodiment of the invention. As depicted, the controller 50 is a part of the ABF system 20 for making on-site peracid chemistry formulations as described by various embodiments herein. The controller 50 may also be described as a software platform or as comprising a software platform. As one skilled in the art will ascertain, the ABF system 20 employing a controller system 50 is not limited to the particular embodiment depicted in FIG. 5.

In some aspects the controller 50 may include various components, including for example, a display screen 52 to assist a user in selecting the various parameters selectable by a user according to the invention. For example, a user views a display screen 52 to view the options available for a particular generation mode of a desired peracid formulation and any other options for user selection as one skilled in the art will ascertain based upon the description of the invention. Concomitant with the controller and software 50 are user-friendly instructions for use displayed on the display screen 52. In additional aspects, the controller 50 may further include a means for manually starting/stopping any of the same functions, including for example a manual switch panel 56 for the same. In addition to manual controls depicted as manual switch panels 56 in FIG. 5, the controller 50 preferably also comprises means for selecting 54 options displayed for a user to select on the display screen 52. These and other means for a user to select the various embodiments of the invention are encompassed in the various embodiments of the controller 50.

The controller 50 provides a user or system the flexibility and means to select a generation mode for a desired peracid formulation for on-site generation according to the invention. The controller provides significant user flexibility to generate chemistries for particular user-identified purposes, such as selecting the peracid formulation and/or the desired volume of the formulation for on-site generation. The software utilized by the controller 50 may further determine the timing, sequencing and/or selection of feeding raw materials 28 (including sugar esters 24) into the system, mixing time and total reaction time required for production of the user- or system-selected peracid formulation.

Figure 6A:
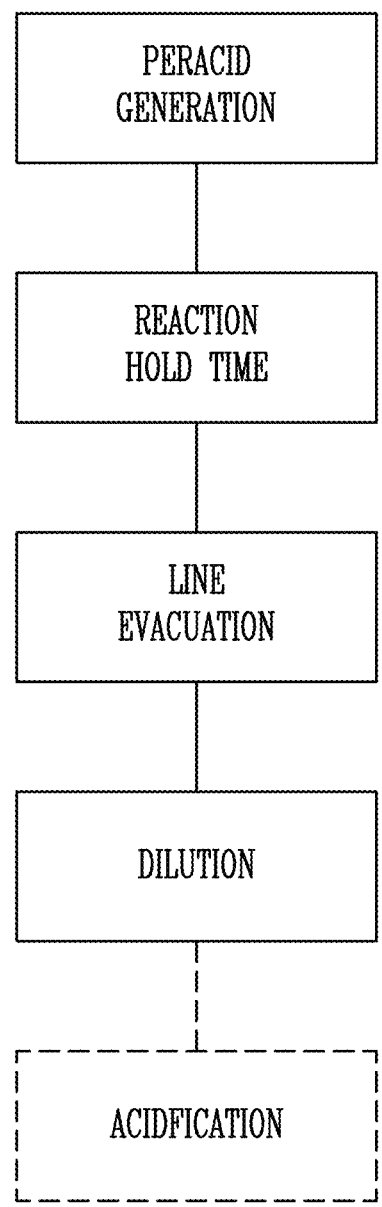
FIGS. 6A-B show diagrams of an embodiment of an adjustable biocide formulator apparatus according to the invention, including description of the dosing of raw starting materials (e.g. reagents) for the generation of peracid chemistries according to the invention.
Figure 6B:
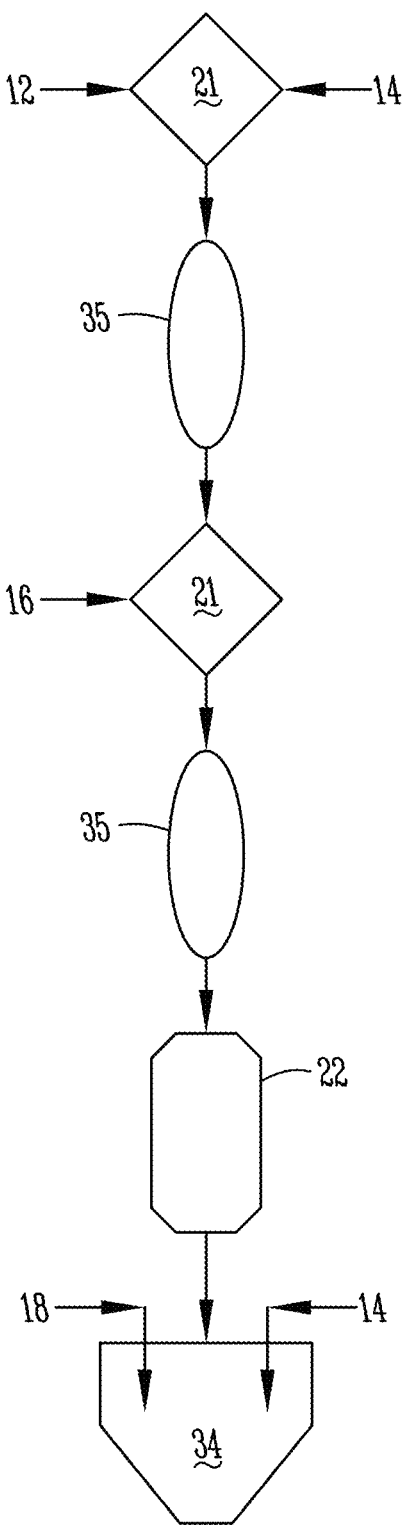

FIGS. 6A and 6B show diagrams of an embodiment of an adjustable biocide formulator apparatus according to the invention, including description of the dosing of raw starting materials (e.g. reagents) for the generation of peracid chemistries according to the invention. In particular, FIG. 6A shows a process flow of methods of making the peracid chemistry using the apparatus according to the invention. As set forth, methods of the invention include the steps of peracid generation, a period of reaction holding time followed by evacuation of the line, dilution with water of the concentrated chemistry and optionally acidification.

FIG. 6B further shows a non-limiting example of a method of peracid chemistry according to FIG. 6A. In the non-limiting example peracid generation includes the injection of raw starting materials (e.g. reagents). In particular, the injection of NaOH 12 and water 14 are combined in injection manifold 21. The injection manifold is not limited according to a particular structure or apparatus. According to a preferred embodiment, the caustic is diluted to a concentration of less than or equal to about 20% by weight. The NaOH 12 and water 14 are preferably homogenized or mixed by passing through a mixer 35. Thereafter, the ester premix or ester and peroxide 16 are injected into another injection manifold 21 of the system. According to this aspect of the invention the ester premix or ester and peroxide are added to the dilute NaOH for improved chemistry generation. The ester premix or its individual components 16 are homogenized or mixed 35 with the caustic stream. Following the mixing, the reagents are held for the reaction to go to completion within a reaction manifold 22. Notably, the holding step can occur directly in a dilution tank 34 or optionally in an intermediate reaction manifold 22. Following the reaction hold time the reaction manifold 22 is purged with water then air into a dilution vessel 34 (e.g. line evacuation). Then water 14 is used for the dilution step within the dilution tank 34 to dilute the concentrated chemistry. In a further aspect the diluted chemistry can be acidified using an acid or aqueous acid solution 18 within the dilution vessel 34 (or optionally within the reaction manifold 22—not depicted in the figure). Upon completion of the peracid generation as depicted in FIGS. 6A-B a water source 14 may be used to flush the system at a high flow rate.

Apparatus Dosing

The apparatus of the ABF system overcomes the raw material feed design challenge of accurately dosing raw materials. According to the invention, liquid based raw materials must be dosed into reaction vessel(s) quickly. For example, according to an embodiment of the invention, the sugar ester is the limiting reaction ingredient and requires accurate dispensing of the raw material. An example of a suitable sugar ester is sorbital octanoate and/or glyceryl octanoate, which are viscous liquids that are difficult to accurately measure As a result, pump selection is critical and accommodating pump characteristics with software is a critical embodiment of the ABF system.

The dispensing precision required to prepare continuous amounts of the chemistry is less critical than with small batch preparation. Regardless, the apparatus of the ABF system provides feed pumps to reduce the presence of air bubbles in the delivery line to ensure accurate dosing of raw starting materials, including sugar esters, resulting in decreased variation in volumetric flow of reagents. In addition to the reduction of air bubbles in a delivery line, the dispensing precision according to the invention delivers the reagents at a constant flow rate over long durations of time, thereby reducing and/or eliminating the need for recalibration of the apparatus.

According to an alternative embodiment of the invention, a viscosity modifier may be added to the sugar ester. A viscosity modifier is a further example of a suitable raw material 28 according to the invention. Viscosity modifiers according to the invention may be used to adjust the rheology of a reagent in order to reduce the viscosity to make a raw material more suitable for use in the apparatus and system according to the invention, namely rendering the raw material significantly easier to pump. A skilled artisan will appreciate, based on the disclosure of the present invention, additional dosing modifications of the ABF system are encompassed within the scope of the present invention.

Apparatus Rinsing

Rinsing of the ABF system has an impact on yield. According to an embodiment of the invention, adequate rinsing of the reaction manifold and/or feed pump lines occurs. According to a preferred embodiment of the invention, the control software of the ABF system may be used to establish a process for system rinsing both reaction manifold and/or feed pump lines at scheduled increments. Remaining water after rinsing or flushing does not have a negative impact on the system. Water remaining in the mixing manifold imparts a dilution factor for which the dilution factor can be accommodated in the formulation. However, reaction intermediates must be rinsed from the system, as any reacted chemistry not flushed impacts the yield of subsequently produced chemistry. This is a result of residual reaction intermediates in the system imparting unknown actives concentration due to the instability of the product at high pH over time. In addition, according to an embodiment an air-purge may be further employed after rinsing of the apparatus according to the invention, which as one skilled in the art will appreciate effectively removes nearly all liquid content from the manifold after a water rinse.

Compositions

The embodiments of the invention are suitable for generating the peroxycarboxylic acid chemistries (as well as the anion peroxycarboxylic acid forming compositions) which are disclosed in further detail in the related U.S. patent application Ser. Nos. 61/427,965, 13/331,304 and 13/331,486, entitled In Situ Generation of Peroxycarboxylic Acids at Alkaline pH and Methods of Use Thereof, which are herein incorporated by reference in its entirety. In addition to the chemistries generated, these applications incorporated by reference further disclose the particular raw starting materials (e.g. reagents) suitable for use in the ABF systems according to the invention to generate the particular chemistries.

In some embodiments, the system according to the present invention produces peroxycarboxylic acid forming compositions or peroxycarboxylic acid compositions for use in a variety of cleaning applications. The compositions have enhanced stability. According to an embodiment of the invention, the peroxycarboxylic acid forming compositions are stable for up to 24 hours providing suitable stability for on-site generation and usage for a variety of cleaning applications. According to a further embodiment, the peroxycarboxylic acid compositions are stable for up to at about 7 to 10 days.

In some aspects, the present disclosure relates to peroxycarboxylic acid forming compositions. That is, the compositions are capable of generating peroxycarboxylic acids in situ, in a non-equilibrium reaction. Surprisingly, it has been found that the optimum pH for the generation of peroxycarboxylic acid compositions is greater than about 12, or pH greater than about 13. It has also been found that mixed peroxycarboxylic acid compositions, viz. compositions that form two or more peroxycarboxylic acids, can be generated in situ in accordance with the methods disclosed herein. Peroxycarboxylic (or percarboxylic) acids generally have the formula $R(CO_3H)n$, where, for example, R is an alkyl, aryl alkyl, cycloalkyl, aromatic, or heterocyclic group, and n is one, two, or three, and named by prefixing the parent acid with peroxy. The R group can be saturated or unsaturated as well as substituted or unsubstituted.

In an embodiment of the invention the peroxycarboxylic acid forming compositions comprise individual reagents combined according to the invention. These reagents are described herein individually along and include at least one ester of a polyhydric alcohol and a C1 to C18 carboxylic acid, an oxidizing agent, a source of alkalinity, solvents, and other functional groups. An acidulant is also described herein as a reagent to be added to the compositions after the formation of the percarboxylic acid(s). Alternatively, as described herein, there may be benefits to providing the reagents in various premix formulations to decrease the number of reagents and/or increase the simplicity of the invention. Each of these embodiments are described in further detail herein.

Esters

In some aspects, the compositions include an ester of a polyhydric alcohol and a C1 to C18 carboxylic acid. According to an embodiment, the polyhydric alcohol may also include a sugar alcohol. The compositions can also include more than one or a mixture of esters of a polyhydric alcohol and a C1 to C18 carboxylic acid. For example, in some embodiments, the compositions include two, three or four esters. When more than one ester is present, the esters can be different. For example, in some embodiments, the compositions can include a first ester of a polyhydric alcohol and a C1 to C4 carboxylic acid, and a second ester of a polyhydric alcohol and a C5 to C11 carboxylic acid. For further example, in some embodiments, the compositions can include a first ester of a polyhydric alcohol and a C1 to C18 carboxylic acid in a mono, di or tri-formation, and a second ester of a polyhydric alcohol and a C1 to C18 carboxylic acid in a mono, di or tri-formation. One skilled in the art will appreciate the various combinations of esters that can be used for the compositions according to the invention.

An example of a suitable ester for use according to the invention is glycerol octanoate. Glycerol octanoate has multiple ester components and others, including glycerol monooctanoate, glycerol dioctanoate, glycerol trioctanoate and others (glycerin, fatty acid, water). An estimated component percentage of each is approximated at about 39.6% glycerol monooctanoate, 24.5% glycerol dioctanoate, 1.42% glycerol trioctanoate and 34.5% of the others (glycerin, fatty acid, water).

The use of various forms of an ester (e.g. mono, di and/or tri-formations) to comprise a mixture of esters will impact the peracid yield of a particular composition according to the invention. For example, the various forms of the ester will have different kinetics in generating the peracids according to the methods of the invention. For example, in one aspect, a monooctanoate glycerol ester is faster in generating peracid than the di- or trioctanoate glycerol esters. In addition, the selection of the various forms of an ester will be further impacted by the water solubility of the compositions and whether any additional ingredients are combined to affect solubility (e.g. solvents) that would favor the use of less soluble ester forms (e.g. tri-formations). Accordingly, one skilled in the art of reaction kinetics will ascertain the benefits of using various combinations or mixtures of esters according to the compositions and methods of the invention.

The esters for use in the present invention include esters of polyhydric alcohols with carboxylic acid based leaving groups. A variety of carboxylic acids can be included. Carboxylic acids generally have the formula R(COOH)n, where, for example, R is an alkyl, aryl alkyl, cycloalkyl, aromatic, or heterocyclic group, and n is one, two, or three. In some embodiments, the carboxylic acid leaving group is a $C_5$ to $C_{11}$ carboxylic acid. In some embodiments, the carboxylic acid leaving group is a $C_1$ to $C_4$ carboxylic acid. In other embodiments, the compositions include two esters of polyhydric alcohols, each ester having a different carboxylic acid leaving group. For example, the compositions can include a polyhydric alcohol ester with a C1 to C4 carboxylic acid leaving group, and also include a polyhydric alcohol ester with a C5 to C11 carboxylic acid leaving group.

Examples of suitable carboxylic acids include, but are not limited to, formic, acetic, propionic, butanoic, pentanoic, hexanoic, heptanoic, octanoic, nonanoic, decanoic, undecanoic, dodecanoic, as well as their branched isomers, lactic, maleic, ascorbic, citric, hydroxyacetic, neopentanoic, neoheptanoic, neodecanoic, oxalic, malonic, succinic, glutaric, adipic, pimelic subric acid, and mixtures thereof.

Without wishing to be bound by any particular theory, it is thought that the esters included in the compositions undergo a perhydrolysis reaction, thereby forming the peroxycarboxylic composition. An exemplary perhydrolysis reaction in accordance with the present disclosure is illustrated below:

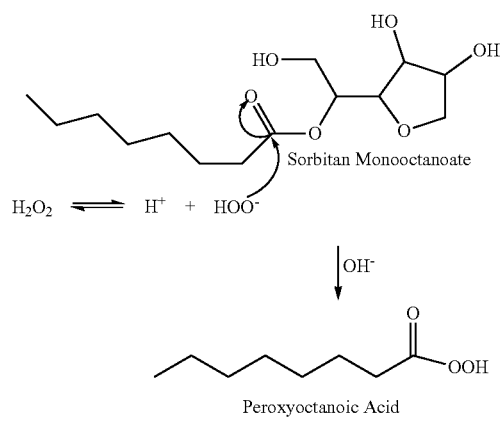

As can be seen from this illustration, it is thought the oxidizing agent, $H_2O_2$, perhydrolyzes the ester bond, thereby forming the percarboxylic acid corresponding to the cleaved carboxylic acid group. In contrast to an acid catalyzed equilibrium reaction, the reaction is stoichiometric, i.e. no excess amounts of the reactants are required for the reaction. The kinetics of the reaction are pH dependent, and the reaction can reach the maximum yield in the order of minutes. Esters suitable for use include, but are not limited to, monooctanoic glyceride, dioctanoic glyceride, trioctaonoic glyceride, polyglycerol octanoate, sorbitan monooctanoate, sorbitan dioctanoate, sorbitan trioctanoate, laurate sucroside and mixtures and derivatives thereof.

The compositions include the esters in an amount sufficient to generate the desired amount of percarboxylic acid. In some embodiments, the compositions include about 0.01 wt-% to about 95 wt-% of the ester, about 0.1 wt-% to about 50 wt-% of the ester, or about 1 wt-% to about 10 wt-% of the ester. In some embodiments, more than one ester is present in the compositions. Each ester can be present in the compositions at the above stated weight percents.

Unlike conventional acid catalyzed equilibrium peroxycarboxylic acid forming compositions, the compositions of the present invention can be formed using a non-equilibrium perhydrolysis reaction. Thus, an excess amount of the starting reagents is not needed. Accordingly, after formation of the peroxycarboxylic acid, the compositions contain less carboxylic acid and more peroxycarboxylic acid than an equivalent equilibrium reaction. In some embodiments, the compositions contain about 1 part percarboxylic acid for every about 1 part carboxylic acid after perhydrolysis, or about 6 part percarboxylic acid for every about 1 part carboxylic acid after perhydrolysis. In some embodiments, the compositions are free of or substantially free of carboxylic acids after the perhydrolysis reaction.

Alkalinity Source

The compositions also include a source of alkalinity. The source of alkalinity can include, but is not limited to, an alkaline metal hydroxide, an alkaline earth metal hydroxide, an alkali metal silicate, an alkali metal carbonate, borates and mixtures thereof. Suitable alkaline metal hydroxides include, but are not limited to, sodium hydroxide, potassium hydroxide and mixtures thereof. Suitable alkaline earth metal hydroxides include, but are not limited to, magnesium hydroxide, calcium hydroxide and mixtures and derivatives thereof. Suitable alkali metal silicates include but are not limited to, sodium silicate and derivatives thereof. In other embodiments, an alkali metal carbonate can be used as a source of alkalinity. For example, in some embodiments, sodium carbonate, sodium bicarbonate or mixtures and derivatives thereof can be used.

The source of alkalinity can be present in the compositions in an amount sufficient to provide the desired pH. In some embodiments, the compositions have a pH greater than about 12, greater than about 12.5, or greater than about 13. In some embodiments, the alkaline source is present in the composition from about 0.001 wt-% to about 50 wt-%, from about 1 wt-% to about 30 wt-%, or about 10 wt-% to about 25 wt-%. In some embodiments, the alkaline source is present at from about 25 wt-% to about 50 wt-% of the composition. It is to be understood that all ranges and values between these ranges and values are encompassed by the present disclosure.

Oxidizing Agent

The compositions also include an oxidizing agent. The oxidizing agent may include a peroxide source. Oxidizing agents suitable for use with the compositions include the following types of compounds or sources of these compounds, or alkali metal salts including these types of compounds, or forming an adduct therewith: hydrogen peroxide, urea-hydrogen peroxide complexes or hydrogen peroxide donors of: group 1 (IA) oxidizing agents, for example lithium peroxide, sodium peroxide; group 2 (IIA) oxidizing agents, for example magnesium peroxide, calcium peroxide, strontium peroxide, barium peroxide; group 12 (IIB) oxidizing agents, for example zinc peroxide; group 13 (IIIA) oxidizing agents, for example boron compounds, such as perborates, for example sodium perborate hexahydrate of the formula $Na_2[B_2(O_2)_2(OH)_4].6H_2O$ (also called sodium perborate tetrahydrate); sodium peroxyborate tetrahydrate of the formula $Na_2B_2(O_2)_2[(OH)_4].4H_2O$ (also called sodium perborate trihydrate); sodium peroxyborate of the formula $Na_2[B_2(O_2)_2(OH)_4]$ (also called sodium perborate monohydrate); group 14 (IVA) oxidizing agents, for example persilicates and peroxycarbonates, which are also called percarbonates, such as persilicates or peroxycarbonates of alkali metals; group 15 (VA) oxidizing agents, for example peroxynitrous acid and its salts; peroxyphosphoric acids and their salts, for example, perphosphates; group 16 (VIA) oxidizing agents, for example peroxysulfuric acids and their salts, such as peroxymonosulfuric and peroxydisulfuric acids, and their salts, such as persulfates, for example, sodium persulfate; and group VIIa oxidizing agents such as sodium periodate, potassium perchlorate. Other active inorganic oxygen compounds can include transition metal peroxides; and other such peroxygen compounds, and mixtures thereof.

In some embodiments, the compositions of the present invention employ one or more of the inorganic oxidizing agents listed above. Suitable inorganic oxidizing agents include ozone, hydrogen peroxide, hydrogen peroxide adduct, group IIIA oxidizing agent, or hydrogen peroxide donors of group VIA oxidizing agent, group VA oxidizing agent, group VIIA oxidizing agent, or mixtures thereof. Suitable examples of such inorganic oxidizing agents include percarbonate, perborate, persulfate, perphosphate, persilicate, or mixtures thereof.

In some embodiments, the oxidizing agent includes hydrogen peroxide, or a source or donor of hydrogen peroxide. In other embodiments, the oxidizing agent includes a peroxide source selected from a percarbonate, a perborate urea hydrogen peroxide, PVP-peroxides and mixtures thereof.

The compositions may contain an effective amount of an oxidizing agent. In some embodiments, the compositions include about 0.001 wt-% to about 60 wt-% of the oxidizing agent, or about 1 wt-% to about 25 wt-% of the oxidizing agent. In some embodiments, the compositions include about 30 wt-% to about 50 wt-% of the oxidizing agent. It is to be understood that all ranges and values between these ranges and values are encompassed by the present invention.

Solvent

In some embodiments, the compositions of the invention further include a solvent. In some embodiments, the solvent is water. The water may be provided by the use of aqueous reagents, viz. oxidizing agent, alkalinity source. In other embodiments, an additional amount of water is added to the compositions. The compositions may be free of or substantially free of any added water. A non-aqueous solvent may also be used in the compositions. For example, in some embodiments, an alcohol is included as a solvent in the compositions.

The compositions may include an effective amount of solvent. In some embodiments, the compositions may include about 10 wt-% to about 99 wt-% of a solvent, or about 20 wt % to about 80 wt-% of a solvent. In other embodiments, the compositions may include more than about 30 wt-%, more than about 50 wt-%, more than about 60 wt-% or more than 70% of a solvent. It is to be understood that all values and ranges between these values and ranges are encompassed by the present invention.

Eliminated Functional Ingredients

Unlike conventional equilibrium based peroxycarboxylic acid compositions, the compositions disclosed herein are formed from a non-equilibrium reaction. Further, the composition disclosed herein can be used immediately after generation. Thus, many of the additional ingredients required in equilibrium based compositions do not need to be included in the present compositions. In some embodiments stabilizing agents are preferred for certain compositions according to the invention and provide benefits. However, beneficially, the use of non-equilibrium chemistry according to the present invention optionally provides that the compositions can be free of, or substantially free of a stabilizing agent.

Stabilizing agents are commonly added to equilibrium peroxycarboxylic acid compositions to stabilize the peracid and hydrogen peroxide and prevent the decomposition of these constituents within the compositions. Various embodiments of the invention do not require the use of at least one or more of such stabilizing agents. Examples of stabilizing agents may include for example, surfactants, couplers, hydrotropes, acid catalysts and the like that are conventionally used in equilibrium peracid compositions to stabilize and improve shelf life of the composition.

Further examples of stabilizing agents include, for example, chelating agents or sequestrants. Such sequestrants include, but are not limited to, organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, aminocarboxylic acids, or heterocyclic carboxylic acids, e.g., pyridine-2,6-dicarboxylic acid (dipicolinic acid). Dipicolinic acid, 1-hydroxy ethylidene-1,1-diphosphonic acid (CH3C(PO3H2)2OH) (HEDP) are further example of stabilizing agents.

Additional examples of stabilizing agents commonly used in equilibrium chemistry to stabilize the peracid and hydrogen peroxide and/or prevent the premature oxidation of the composition include phosphonic acid or phosphonate salt. Phosphonic acids and phosphonate salts include HEDP;

ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; picolinic, dipicolinic acid or mixtures thereof. In some embodiments, organic phosphonates, e.g., HEDP are well known as used stabilizing agents.

Exemplary commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino(tri(methylenephosphonic acid)), (N[CH$_2$PO$_3$H$_2$]$_3$), available from Monsanto as DEQUEST® 2000; ethylenediamine[tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM. Further exemplary sequestrant can be or include aminocarboxylic acid type sequestrant. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and alanine-N,N-diacetic acid; and the like; and mixtures thereof. Still further sequestrants include polycarboxylates, including, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

Further, unlike conventional equilibrium based peroxycarboxylic acid compositions, the present compositions can also be free of, or substantially free of surfactants. This is especially advantageous for compositions incorporating C5 to C18 peroxycarboxylic acids. That is, under perhydrolysis conditions, the C5-C18 peroxycarboxylic acid anions generated are water soluble. If the anions (e.g. peroxycarboxylic acid-forming compositions) are acidified for end use applications, the concentrations of peroxycarboxylic acids are below the water solubility limit of the peroxycarboxylic acids. Thus, couplers are not needed to couple the peroxycarboxylic acids in solution.

Additional Functional Ingredients

The compositions may also include additional functional ingredients. Additional functional ingredients suitable for use in the present compositions include, but are not limited to, acidulants, hydrotropes, dispersants, antimicrobial agents, optical tracers, solidification agent, aesthetic enhancing agent (i.e., colorant (e.g., pigment), odorant, or perfume), among any number of constituents which can be added to the composition. For example, suitable functional ingredients for various embodiments of the invention are hydrotropes, which may be desired for producing clear compositions or dispersants which are more efficient in producing homogeneous dispersions. Such adjuvants can be preformulated with the present compositions or added to the compositions after formation, but prior to use. The compositions can also contain any number of other constituents as necessitated by the application, which are known and which can facilitate the activity of the present compositions.

Acidulant

In an embodiment, the present compositions can include an acidulant. The acidulant can be added to the compositions after the formation of the percarboxylic acid. That is, an acidulant can be added to the peroxycarboxylic acid concentrate to form an acidified use solution. The acidulant can be effective to form a use composition with pH of about 1 or less. The acidulant can be effective to form a use composition with pH of about 8, about 8 or less, about 7, about 7 or less, about 6, about 6 or less, about 5, about 5 or less, or the like. In some embodiments, the acidulant is present at an amount effective to form a use solution with a pH of about 6 to about 8, about 1 to about 8, or about 1 to about 5. In a further embodiment, the acidulant may be added to a semi-diluted reaction solution to produce metastable peracid composition.

Any suitable acid can be included in the compositions as an acidulant. In an embodiment the acidulant is an acid or an aqueous acidic solution. In an embodiment, the acidulant includes an inorganic acid. In some embodiments, the acidulant is a strong mineral acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, cumene sulfonic acid, benzene sulfonic acid, formic acid, acetic acid, mono, di, or tri-halocarboyxlic acids, picolinic acid, dipicolinic acid, and mixtures thereof. In some embodiments, the compositions of the present invention are free or substantially free of a phosphorous based acid.

In an embodiment, the acidulant includes a carboxylic acid with pK$_a$ less than 5. Suitable carboxylic acids with pK$_a$ less than 5 include acetic acid, hydroxyacetic acid, hydroxypropionic acid, other hydroxycarboxylic acids, mixtures thereof, or the like. Such an acidulant is present at a concentration where it does not act as a solubilizer. In some embodiments, the compositions are free of, or substantially free of a carboxylic acid.

In certain embodiments, the present composition includes about 0.001 to about 50 wt-% acidulant, about 0.001 to about 30 wt-% acidulant, about 1 to about 50 wt-% acidulant, about 1 to about 30 wt-% acidulant, about 2 to about 40 wt-% acidulant, about 2 to about 10 wt-% acidulant, about 3 to about 40 wt-% acidulant, about 5 to about 40 wt-% acidulant, about 5 to about 25 wt-% acidulant, about 10 to about 40 wt-% acidulant, about 10 to about 30 wt-% acidulant, about 15 to about 35 wt-% acidulant, about 15 to about 30 wt-% acidulant, or about 40 to about 60 wt-% acidulant. The composition can include any of these ranges or amounts not modified by about.

Premix Formulations

In an embodiment, the reagents described herein (e.g. at least one ester of a polyhydric alcohol and a carboxylic acid, source of alkalinity, oxidizing agent) may be combined into various premix formulations to reduce the number of raw starting materials required for the methods and compositions and further simplify the methods of the invention. According to such an embodiment the providing of premix formulations ensures consistent and stable delivery of reagents.

Premix formulations suitable for use according to the invention may comprise, consist of and/or consist essentially of at least one ester, an oxidizing agent and mixtures thereof. Premix formulations suitable for use according to the invention may comprise, consist of and/or consist essentially of at least one ester, an oxidizing agent, a solvent and mixtures thereof. Premix formulations suitable for use according to the invention may also comprise, consist of and/or consist essentially of at least one ester, an oxidizing agent, water, solvents, dispersing agents, and mixtures thereof.

As one skilled in the art will ascertain the use of premixes employs additional function ingredients for purpose of stabilizing the premix concentrate for use in the compositions and methods according to the invention. For example, hydrotropes, dispersing agents and/or other solvents may be desirable for maintaining the solubility and stability of a particular concentrated premix. The use of any couplers or dispersing agent (such as a surfactant) within a premix formulation is distinct from the use of surfactants in the conventional generation and storage of peracid chemistries, wherein couplers are critical to establishing and maintaining a stable, clear solution of the generated peracid chemistry.

According to the invention, the use of dispersing agents alone within a concentrated premix formulation does not stabilize the premix composition. Rather the dispersing agents are provided in an amount suitable for providing meta-stable peracid compositions generated from the premix after acidification, before further dilution for application. The most efficient dispersing agents were found to be anionic surfactants, and this type of surfactant is known to have high foaming profile. For applications which involves mechanical actions (e.g. CIP sanitizing), the high foam property of the composition is undesirable. Thus, in addition to economic reason, it is preferred to use a minimum amount of the dispersing agent to achieve a meta-stable peracid composition to meet the application of use requirements.

According to an embodiment of the invention less than about 10 ppm, preferably less than about 9 ppm, less than about 8 ppm, less than about 7 ppm, less than about 6 ppm, less than about 5 ppm, less than about 4 ppm, less than about 3 ppm, less than about 2 ppm, or less than about 1 ppm of a dispersing agent is included in the generated peracid chemistry as a result of the use of a surfactant dispersing agent in a concentrated premix formulation according to the invention. This is distinct from the level of surfactants in use solutions of a traditional peracid chemistry, where the amounts of surfactants are normally in excess of about 50 ppm, in excess of about 60 ppm, in excess of about 70 ppm, in excess of about 80 ppm, in excess of about 90 ppm, or in excess of about 100 ppm.

According to a further embodiment of the invention less than about 2% dispersing agent is present in the premix composition, wherein at least about 5%, about 6%, about 7%, about 8% or about 9% are required to provide the stable, clear solution of a generated peracid chemistry when acidified. This is distinct from the generated peracid chemistry according to the invention wherein a meta stable chemistry is generated. Although not wishing to be limited to a particular theory of mechanism of action of the invention, the generated meta-stable composition is a milky colored composition having stability for at least a few hours.

According to an embodiment of the invention, the use of a solvent (e.g. ethanol) is an efficient way to make a stable premix composition. Solvents suitable for the concentrated premix formulations according to the invention include, for example, organic solvents such as alcohol, ether or ketone. Preferably, the solvent is a water soluble alcohol, such as ethanol, methanol, propanol, isopropanol and/or butanol.

Beneficially, the use of concentrated premix formulation still does not require the use of any chelators and/or stabilizers. As a result, regardless of whether individual reagents or concentrated premix formulations are utilized according to the invention, both the reagents and the peracid compositions generated according to the invention provide sustainable chemistries as a result of the elimination of the use of various stabilizers and/or additional amounts of chemistry required to drive the formation of traditional peracid chemistry. As a result of reduced input of reagents for the compositions according to the invention (e.g. resulting from the use of a non-equilibrium reaction) there is a significantly reduced waste stream (e.g. any reagents and/or percentage of composition not impacting the micro-efficacy of the compositions). Instead the present invention provides increased amounts of post-reaction products (e.g. peracids) with decreased amounts of unreacted reagents.

In an aspect of the invention, a premix formulation may deliver the ester of a polyhydric alcohol and a carboxylic acid and the oxidizing agent. In one aspect a premix formulation includes an ester of a polyhydric alcohol and a carboxylic acid, an oxidizing agent and a dispersing agent. In another aspect a premix formulation includes an ester of a polyhydric alcohol and a carboxylic acid, an oxidizing agent, a dispersing agent and water.

Suitable dispersing agents for use according to the concentrated premix formulations of the invention include polymers, surface active agents or any compounds which will help to achieve a meta-stable solution after the ester perhydrolysis through the interaction with the peroxy fatty acids generated through perhydrolysis. These may include, for example, sulfonated oleic acids (SOA), 1-octanesulfonic acid (NAS), sodium lauryl sulfonates (SLS) and the like. In another aspect a premix formulation includes an ester of a polyhydric alcohol and a carboxylic acid, an oxidizing agent and a solvent. Ethanol and methanol are examples of suitable solvents for use in stabilizing the concentrated premix formulation according to the invention. The use of the solvent in certain embodiments obviates the use of a dispersing agent for premix stability. However, in alternative embodiments a premix formulation may include an ester of a polyhydric alcohol and a carboxylic acid, an oxidizing agent, a dispersing agent and a solvent. Without wishing to be limited to a particular theory or mechanism of action of the invention, the combined use of a dispersing agent and a solvent within a concentrated premix formulation reduces the overall need for a surfactant dispersing agent in the premix composition.

In still another aspect a concentrated premix formulation includes an oxidizing agent and a dispersing agent.

In certain embodiments, the concentrated premix composition includes about 0.001 to about 90 wt-% ester of the polyhydric alcohol and a carboxylic acid, about 0.1 to about 90 wt-% ester, about 1 to about 75 wt-% ester, about 10 to about 75 wt-% ester, about 25 to about 75 wt-% ester, about 30 to about 70 wt-% ester, or about 30 to about 65 wt-% ester.

In certain embodiments, the concentrated premix composition further includes about 0.001 to about 99 wt-% oxidizing agent, about 0.1 to about 95 wt-% oxidizing agent, about 1 to about 90 wt-% oxidizing agent, about 2.5 to about 60 wt-% oxidizing agent, about 5 to about 50 wt-% oxidizing agent, or about 10 to about 40 wt-% oxidizing agent.

In certain embodiments, the concentrated premix composition further includes about 0.001 to about 50 wt-% dispersing agent, about 0.1 to about 40 wt-% dispersing agent, about 1 to about 30 wt-% dispersing agent, about 5 to about 30 wt-% dispersing agent, about 5 to about 20 wt-% dispersing agent, or about 5 to about 15 wt-% dispersing agent. The amount of dispersing agent is selected to ensure that only enough dispersing agent to obtain a meta-stable solution after perhydrolysis and acidification. Beneficially according to the invention, the premix formulations do not contain sufficient dispersing agent to obtain a one phase premix solution.

In certain embodiments, the concentrated premix composition further includes about 0.001 to about 80 wt-% solvent, about 0.1 to about 40 wt-% solvent, about 1 to about 30 wt-% solvent, about 5 to about 30 wt-% solvent, about 5 to about 20 wt-% solvent, or about 5 to about 15 wt-% solvent. 3 The level of solvent is selected to ensure the sufficient amount to solubilize the ester(s) of polyhydric alcohol in the concentrated premix formulation. As one skilled in the art will ascertain the amount of solvent required for such solubilization will vary depending upon the type and level of ester(s) in the premix composition.

In certain embodiments, the concentrated premix composition further includes about 0.001 to about 90 wt-% water, about 0.1 to about 80 wt-% water, about 1 to about 75 wt-% water, about 5 to about 60 wt-% water, about 10 to about 50 wt-% water, or about 20 to about 40 wt-% water. The premix compositions can include any of these ranges or amounts, including those not modified by about.

The pH of the concentrated premix formulation according to the invention is preferably between 2 and about 10, preferably between about 3 and about 9, and more preferably between about 5 and about 7. Thereafter the pH of the premix formulation is combined with an a source of alkalinity to increase the pH to a pH greater than about 12, greater than about 12.5, or greater than about 13 according to the invention.

Methods of Making Peracid Compositions

In some aspects, the present disclosure provides methods for on-site generation of the peroxycarboxylic acid forming compositions and peroxycarboxylic acid disclosed herein. According to an embodiment of the invention, the methods of on-site generation are particularly suitable for continuous preparation mode of the peroxycarboxylic acid forming compositions and peroxycarboxylic acids.

The method includes combining at least one ester of a polyhydric alcohol and a C1 to C18 carboxylic acid, a source of alkalinity and an oxidizing agent in a reaction manifold. The method may include inputting a user- or system-controlled peroxycarboxylic acid forming composition or peroxycarboxylic acid formulation that is desired for a particular use. The user- or system-controlled input may be put into a control software for an adjustable biocide formulator or generator system, wherein said input formulation selects an individual or mixed peroxycarboxylic acid forming composition or peroxycarboxylic acid and the corresponding volume or mass of the chemistry for onsite generation.

In some embodiments a user controls the input for the on-site chemistry generation. In further embodiments, a system-controlled input may include, for example, a CIP process, bottle washer, aseptic filler, vegetable wash or rinse sink, 3$^{rd}$ sink sanitizing sink, textile bleaching process and combinations thereof.

In some embodiments, the user- or system-input selects either a single or multiple reaction vessel mode for the peroxycarboxylic acid and/or mixed peroxycarboxylic acid or peroxycarboxylic acid forming composition generation. As a result of the reaction vessel mode selected by the input, the addition of the reaction reagents, including at least the esters, source of alkalinity and oxidizing agent, may be added in parallel or sequentially. The reagents can be combined in any suitable manner according to the invention and mixed for an amount of time effective to form the desired percarboxylic acid forming composition or percarboxylic acid concentration.

According to the invention, reagents may be added substantially simultaneously to a reaction manifold, and mixed through the circulation or flow of the reagents through the reaction manifold (e.g. variable length) for an amount of time effective to form the desired concentration. Alternatively, reagents may be added sequentially to the reaction manifold or to different sections/locations within the reaction manifold. Still further, reagents may be provided from reaction manifold into an additional reaction manifold or a reservoir (e.g. dilution tank).

In some embodiments, the pH of the reaction mixture is greater than about 12. In other embodiments, the reaction mixture is greater than about 12.5, or greater than about 13.

According to an embodiment of the invention, the reagents are mixed in the reaction manifold for a period of time sufficient for the perhydrolysis reaction to occur. In some embodiments, the reagents are mixed for about 5 to about 30 minutes. In other embodiments, the reagents are mixed for about 10, about 15, about 20, or about 25 minutes. The mixing may further take place using means of altering the laminar flow of the reagents through the reaction manifold, alternating the pressure differential within the reaction manifold, or according to additional embodiments disclosed herein to ensure homogeneous blending of reagents.

In additional preferred embodiments the mix order of reagents are controlled to produce a consistent output of peracid chemistry without any fouling (e.g. precipitation) of the reagents. In one aspect of the invention, the source of alkalinity (e.g. sodium hydroxide or caustic soda) is combined with water (e.g. diluted) prior to the addition of the ester source. As disclosed herein the ester source can further be provided in an ester premix (e.g. ester/peroxide premix).

The concentration of reagents, in addition to mixing order, can further be used to control the production of the percarboxylic acid composition. In a preferred embodiment, the concentration of the source of alkalinity is diluted to produce a consistent output of chemistry without any fouling (e.g. precipitation) of the reagents. In one aspect the concentrated alkaline solution (e.g. NaOH) is diluted with a water source before the ester component is combined with the reagents. Although not intending to be limited according to any theory of the invention and/or mechanism of action, the invention demonstrates superior chemistry generation when a system delivers a source of alkalinity (e.g. NaOH solution) that is no more than about 50%, preferably no more than about 40% on an actives basis before combining with the ester reagent to initiate the peracid production reaction.

According to preferred methods of making the peracid chemistry, an ex-situ ABF generator system using an injection manifold to combine an alkaline source, an ester precursor, a peroxygen source and optionally water for production of a peroxy acid is used. Preferably the alkaline source is caustic soda, wherein the caustic stream feeding the manifold is diluted. In an aspect the caustic can be diluted within the manifold to the target concentration of less than about 50%, preferably less than about 40% by weight. In an additional embodiment, the ester is added to the system downstream (e.g. after the addition of the diluted NaOH solution).

In an embodiment, the extent of the ester perhydrolysis reaction is measured using one or more measurement devices. Suitable measurement devices measures one or more reaction kinetics or system operations, including for example fluorescence, weight, flow, capacitive level, pH, oxidation reduction potential, pressure, temperature and combinations thereof. Measurement devices may be used to determine the need and/or timing to add an acid or aqueous acidic solution to dilute the peroxycarboxylic acid forming composition to form the peroxycarboxylic acid composition. In some embodiments the addition of an acid or aqueous acidic solution decreases the pH of the reaction mixture from greater than about 12 to a neutralized pH of about 1.0 to about 8.0.

In an embodiment of the invention, the peroxycarboxylic acid forming composition is dispensed for use in a cleaning process. An acid or aqueous acidic solution may be added to the peroxycarboxylic acid forming composition outside of the system according to the invention.

Preferably, the ABF system, including the reaction manifolds, are cleaned at scheduled increments. Rinsing of the ABF system is expected to have an impact on yield of the peroxycarboxylic acid forming compositions. According to an embodiment of the invention, the system is rinsed (e.g. feed pump lines flushed) with warm/hot water at regularly scheduled increments (e.g. every 12 hours) or after a continuous system is shut down, and/or at regularly schedules intervals to comply with regulatory requirements (e.g. sanitizing regulations), as one skilled in the art shall ascertain. A particularly suitable embodiment of the invention forms a mixed percarboxylic acid composition by using more than one ester of a polyhydric alcohol and a C1 to C18 carboxylic acid as starting reagents.

For example, in some embodiments, a mixed percarboxylic acid composition including peracetic acid and peroctanoic acid is formed. To form this composition, an ester of a polyhydric alcohol and a C1 carboxylic acid is combined with an ester of a polyhydric alcohol and a C8 carboxylic acid, a source of alkalinity, and an oxidizing agent. When forming a mixed peracid composition, the order of addition can be varied depending on the reaction conditions. For example, in some embodiments, all of the reagents can be combined and mixed in one step. Alternatively, in some embodiments, one of the esters can be added to a reaction manifold, with an oxidizing agent, and a source of alkalinity added sequentially. This mixture can be allowed to react for an effective amount of time, prior to the second ester being added to the reaction manifold to form the second peracid composition. Preparing the mixed percarboxylic acid system in a stepwise manner also allows for control of the reaction temperature. For example, by splitting the perhydrolysis reactions into two steps, the overall temperature of the reaction mixture is lower.

In some aspects of the invention, the order of addition and time for reaction can be varied according to the desired percarboxylic acid composition. That is, the reaction can be controlled so as to favor the reaction conditions for formation of each of the percarboxylic acids individually. For example, if it is known that one of the esters has a kinetically slower perhydrolysis reaction rate, that ester can be added to the reaction manifold first. After an amount of time sufficient to maximize the percarboxylic acid formation of the first ester, the second ester with a kinetically faster perhydrolysis reaction rate can be added to the reaction manifold.

According to additional aspects of the invention, the selected quantity of a desired percarboxylic acid forming composition or percarboxylic acid to be produced continuously according to the invention impacts the reaction kinetics. According to the invention, a user- or system-inputted batch size (i.e. volume) to the ABF system impacts the reaction kinetics. Although not intending to be limited to a particular theory, when generating various quantities of the chemistries with the ABF system according to the invention, not all reactions are linearly time-scaled, such that generation of a larger quantity of chemistry (i.e. hundreds of gallons) may require a different timing sequence depending on the reaction kinetics and various mixing parameters. The present invention accommodates the changes in user- or system-inputted chemistry quantity, such that for different volumes of peracid compositions the time constants for its formulation will vary.

In some aspects, the present disclosure provides methods for forming an antimicrobial and/or disinfecting composition. The methods include providing a mixed peroxycarboxylic acid forming composition. The mixed peroxycarboxylic acid forming composition includes: a first ester of a polyhydric alcohol and a C1 to C18 carboxylic acid, for example a C1 to C4 carboxylic acid; a second ester of a polyhydric alcohol and a C1 to C18 carboxylic acid, for example a C8 to C11 carboxylic acid; a source of alkalinity; and an oxidizing agent. After allowing the reaction mixture to react for a sufficient amount of time, a mixed percarboxylic acid composition is formed. The mixed peroxycarboxylic acid composition is diluted with an acidic aqueous solution. In some embodiments, the mixed peroxycarboxylic acid composition is diluted with an amount of an acidic aqueous solution effective to provide the diluted composition with a pH of about 1.0 to about 8.0.

In other aspects, the present disclosure provides methods for forming an antimicrobial and/or disinfecting composition including a single percarboxylic acid. The methods include providing a peroxycarboxylic acid forming composition. The composition includes: an ester of a polyhydric alcohol and a C1 to C18 carboxylic acid; a source of alkalinity; and an oxidizing agent, wherein said composition has a pH greater than 12. The peroxycarboxylic acid forming composition is then diluted with an acidic aqueous solution. In some embodiments, the diluted acidic peroxycarboxylic acid composition has a pH of about 1.0 to about 8.0.

Any acidic solution can be used to dilute the peroxycarboxylic acid compositions. In an embodiment, the acidulant includes an inorganic acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, benzene sulfonic acid, formic acid, acetic acid, mono, di, or tri-halocarboyxlic acids, picolinic acid, dipicolinic acid, and mixtures thereof. In some embodiments, the compositions of the present invention are free or substantially free of a phosphorous based acid.

Methods Employing Peracid Compositions

In some aspects, the present disclosure includes methods of using the peroxycarboxylic acid forming compositions disclosed herein. In some aspects, the methods of using the compositions employ a chemistry having a pH of from about 0 to about 5 for various antimicrobial and/or bleaching applications. In other aspects, the methods of using the compositions employ a chemistry having a pH of from about 5 to about 9 for various antimicrobial and/or bleaching applications. In still further aspects, the methods of using the compositions employ a chemistry having a pH of from about 5 to about 14 for various bleaching applications.

In some aspects, the present disclosure includes methods of using the continuously generated peroxycarboxylic acid forming compositions and/or peroxycarboxylic acids disclosed herein. Peracid compositions generated according to the embodiments of the invention may be used for a variety of user-identified biocidal and/or anti-microbial purposes. In particular, numerous biocidal and/or anti-microbial applications require increased chemical usage and/or demands. Such large volume and demand applications require an ABF system suitable for continuous chemistry generation.

In some aspects, the continuous on-site generation of peracid compositions in large volumes may be particularly well suited for certain textile care applications for use as a disinfectant and bleach chemistry. The methods of continuous on-site generation may be supplied, for example, directly to a laundry application, such as tunnel washers. Such a chemistry demand would be challenging to manufacture using the batch-mode ABF system. A tunnel washer also has a continuous and periodic demand for chemistry that can be easily generated according to the continuous production methods and systems described herein according to the invention.

In some aspects, the on-site generated peracid compositions may be employed for antimicrobial and/or bleaching methods of use. For example, the invention includes a method for reducing a microbial population, a method for reducing the population of a microorganism on skin, a method for treating a disease of skin, a method for reducing an odor, or a method for bleaching. These methods can operate on an object, surface, in a body or stream of water or a gas, or the like, by contacting the object, surface, body, or stream with a peracid composition of the invention. Contacting can include any of numerous methods for applying a composition, such as spraying the composition, immersing the object in the composition, foam or gel treating the object with the composition, wiping the composition or a combination thereof.

In some aspects, a composition obtained according to the methods and apparatus of the present invention includes an amount of a peracid composition of the present invention effective for killing one or more of the food-borne pathogenic bacteria associated with a food product, including, but not limited to, *Salmonella typhimurium, Salmonella javiana, Campylobacter jejuni, Listeria monocytogenes*, and *Escherichia coli* O157:H7, yeast, and mold. In some embodiments, the compositions obtained according to the methods and apparatus of the present invention include an amount of a peracid composition effective for killing one or more of the pathogenic bacteria associated with a health care surfaces and environments including, but not limited to, *Salmonella typhimurium, Staphylococcus aureus, Salmonella choleraesurus, Pseudomonas aeruginosa, Escherichia coli*, mycobacteria, yeast, and mold. The compositions obtained according to the methods and apparatus of the present invention have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. The compositions obtained according to the methods and apparatus of the present invention, as described above, have activity against a wide variety of human pathogens. The present compositions obtained according to the methods and apparatus of the present invention can kill a wide variety of microorganisms on a food processing surface, on the surface of a food product, in water used for washing or processing of food product, on a health care surface, in a health care environment or the like.

The compositions obtained according to the methods and apparatus of the invention can be used for a variety of domestic or industrial applications, e.g., to reduce microbial or viral populations on a surface or object or in a body or stream of water. The compositions can be applied in a variety of areas including kitchens, bathrooms, factories, hospitals, dental offices, restaurants, clean in place applications, laundry or textile applications and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic.

Suitable soft surfaces include, for example, paper; filter media, hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions obtained according to the methods and apparatus of the invention can also be applied to soft surfaces such as food and skin (e.g., a hand). The present compositions can be employed as a foaming or nonfoaming environmental sanitizer or disinfectant.

The peracid compositions obtained according to the methods and system of the present invention can be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

The compositions can also be used in veterinary products such as mammalian skin treatments or in products for sanitizing or disinfecting animal enclosures, pens, watering stations, and veterinary treatment areas such as inspection tables and operation rooms. The present compositions can be employed in an antimicrobial foot bath for livestock or people. The compositions can also be employed as an antimicrobial teat dip.

In some aspects, the compositions obtained according to the methods and apparatus of the present invention can be employed for reducing the population of pathogenic microorganisms, such as pathogens of humans, animals, and the like. The compositions exhibit activity against pathogens including fungi, molds, bacteria, spores, and viruses, for example, *S. aureus, E. coli*, Streptococci, *Legionella, Pseudomonas aeruginosa*, mycobacteria, tuberculosis, phages, or the like. Such pathogens can cause a variety of diseases and disorders, including mastitis or other mammalian milking diseases, tuberculosis, and the like. The compositions of the present invention can reduce the population of microorganisms on skin or other external or mucosal surfaces of an animal. In addition, the present compositions can kill pathogenic microorganisms that spread through transfer by water, air, or a surface substrate. The composition need only be applied to the skin, other external or mucosal surfaces of an animal water, air, or surface.

The peracid compositions obtained according to the methods and apparatus of the present invention can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like.

Particular foodstuffs that can be treated with compositions of the invention include, but are not limited to, eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

The compositions can also be used to treat waste water where both its antimicrobial function and its oxidant properties can be utilized. Aside from the microbial issues surrounding waste water, it is often rich in malodorous compounds of reduced sulfur, nitrogen or phosphorous. A strong oxidant such as the present invention converts these compounds efficiently to their odor free derivatives e.g. the sulfates, phosphates and amine oxides. These same properties are very useful in the pulp and paper industry where the property of bleaching is also of great utility.

In some aspects, the compositions obtained according to the methods and apparatus of the present invention are useful in the cleaning or sanitizing of containers, processing facilities, or equipment in the food service or food processing industries. The compositions have particular value for use on food packaging materials and equipment, and especially for cold or hot aseptic packaging. Examples of process facilities in which the composition of the invention can be employed include a milk line dairy, a continuous brewing system, food processing lines such as pumpable food systems and beverage lines, etc. Food service wares can be treated with an antimicrobial and/or disinfected with the composition of the invention. For example, the compositions can also be used on or in ware wash machines, dishware, bottle washers, bottle chillers, warmers, third sink washers, cutting areas (e.g., water knives, slicers, cutters and saws), egg washers or the like. Particular treatable surfaces include, but are not limited to, packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The compositions can also be used on or in other industrial equipment and in other industrial process streams such as heaters, cooling towers, boilers, retort waters, rinse waters, aseptic packaging wash waters, and the like. The compositions can be used to treat microbes and odors in recreational waters such as in pools, spas, recreational flumes and water slides, fountains, and the like. The composition can also be used in treating microbes found in aqueous systems associated with petroleum or LP gas recovery or fermentation processes and pulp and paper processes and the like.

A filter containing peracid compositions of the present invention can reduce the population of microorganisms in air and liquids. Such a filter can remove water and air-born pathogens such as *Legionella*.

The compositions obtained according to the methods and apparatus of the present invention can be employed for reducing the population of microbes, fruit flies, or other insect larva on a drain or other surface.

The compositions of the present invention can also be employed by dipping food processing equipment into the use solution, soaking the equipment for a time sufficient to sanitize or destain the equipment, and wiping or draining excess solution off the equipment. The compositions of the present invention may be further employed by spraying or wiping food processing surfaces with the use solution, keeping the surfaces wet for a time sufficient to sanitize the surfaces, and removing excess solution by wiping, draining vertically, vacuuming, etc.

The compositions obtained according to the methods and system of the present invention may also be used in a method of sanitizing hard surfaces such as institutional type equipment, utensils, dishes, health care equipment or tools, and other hard surfaces.

The compositions of the present invention can also be used for laundry or textile applications. The compositions can be employed by rinsing laundry or textile surfaces with the use solution, keeping the surfaces wet for a sufficient time to wash, destain, sanitize, bleach and/or rinse the surface.

The peracid compositions can be applied to microbes or to soiled or cleaned surfaces using a variety of methods. These methods can operate on an object, surface, in a body or stream of water or a gas, or the like, by contacting the object, surface, body, or stream with a composition of the invention. Contacting can include any of numerous methods for applying a composition, such as spraying the composition, immersing the object in the composition, rinsing the composition, foam or gel treating the object with the composition, applying with a wipe system or a combination thereof.

A concentrate or use concentration of a peracid composition obtained according to the methods and apparatus of the present invention can be applied to or brought into contact with an object by any conventional method or apparatus for applying an antimicrobial or cleaning composition to an object. For example, the object can be wiped with, sprayed with, foamed on, and/or immersed in the composition, or a use solution made from the composition. The compositions can be sprayed, foamed, or wiped onto a surface; the composition can be caused to flow over the surface, or the surface can be dipped into the composition. Contacting can be manual or by machine. Food processing surfaces, food products, food processing or transport waters, and the like can be treated with liquid, foam, gel, aerosol, gas, wax, solid, or powdered peracid compositions according to the invention, or solutions containing these compositions.

Other hard surface cleaning applications for the compositions include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like. CIP systems include the internal components of tanks, lines, pumps and other process equipment used for processing typically liquid product streams such as beverages, milk, juices.

A method of sanitizing substantially fixed in-place process facilities includes the following steps. A composition in accordance with various embodiments of the invention is introduced into the process facilities at a temperature in the range of about 4° C. to 60° C. After introduction of the composition, the solution is held in a container or circulated throughout the system for a time sufficient to sanitize the process facilities (e.g., to kill undesirable microorganisms). After the surfaces have been sanitized by means of the present compositions, the solution is drained. Upon completion of the sanitizing step, the system optionally may be rinsed with other materials such as potable water. The compositions can be circulated through the process facilities for 10 minutes or less.

The present methods can include delivering the present composition via air delivery to the clean-in-place or other surfaces such as those inside pipes and tanks. This method of air delivery can reduce the volume of solution required.

Methods for Contacting a Food Product

In some aspects, the present invention provides methods for contacting a food product with compositions according to the invention employing any method or apparatus suitable for applying such compositions. For example, in some embodiments, the food product is contacted by the compositions with a spray of the compositions, by immersion in the compositions, by foam or gel treating with the compositions. Contact with a spray, a foam, a gel, or by immersion can be accomplished by a variety of methods known to those of skill in the art for applying antimicrobial agents to food. Contacting the food product can occur in any location in which the food product might be found, such as field, processing site or plant, vehicle, warehouse, store, restaurant, or home. These same methods can also be adapted to apply the compositions of the present invention to other objects.

The present methods require a certain minimal contact time of the compositions with food product for occurrence of significant antimicrobial effect. The contact time can vary with concentration of the use compositions, method of applying the use compositions, temperature of the use compositions, amount of soil on the food product, number of microorganisms on the food product, type of antimicrobial agent, or the like. The exposure time can be at least about 5 to about 15 seconds. In some embodiments, the exposure time is about 15 to about 30 seconds. In other embodiments, the exposure time is at least about 30 seconds.

In some embodiments, the method for washing a food product employs a pressure spray including compositions of the present invention. During application of the spray solution on the food product, the surface of the food product can be moved with mechanical action, e.g., agitated, rubbed, brushed, etc. Agitation can be by physical scrubbing of the food product, through the action of the spray solution under pressure, through sonication, or by other methods. Agitation increases the efficacy of the spray solution in killing micro-organisms, perhaps due to better exposure of the solution into the crevasses or small colonies containing the microorganisms. The spray solution, before application, can also be heated to a temperature of about 15 to 20° C., for example, about 20 to 60° C. to increase efficacy. The spray stabilized compositions can be left on the food product for a sufficient amount of time to suitably reduce the population of microorganisms, and then rinsed, drained, or evaporated off the food product.

Application of the material by spray can be accomplished using a manual spray wand application, an automatic spray of food product moving along a production line using multiple spray heads to ensure complete contact, or other spray apparatus. One automatic spray application involves the use of a spray booth. The spray booth substantially confines the sprayed compositions to within the booth. The production line moves the food product through the entryway into the spray booth in which the food product is sprayed on all its exterior surfaces with sprays within the booth. After a complete coverage of the material and drainage of the material from the food product within the booth, the food product can then exit the booth. The spray booth can include steam jets that can be used to apply the stabilized compounds of the invention. These steam jets can be used in combination with cooling water to ensure that the treatment reaching the food product surface is less than 65° C., e.g., less than 60° C. The temperature of the spray on the food product is important to ensure that the food product is not substantially altered (cooked) by the temperature of the spray. The spray pattern can be virtually any useful spray pattern.

Immersing a food product in the liquid compositions of the present invention can be accomplished by any of a variety of methods known to those of skill in the art. For example, the food product can be placed into a tank or bath containing the compositions. Alternatively, the food product can be transported or processed in a flume of the compositions. The washing solution can be agitated to increase the efficacy of the solution and the speed at which the solution reduces micro-organisms accompanying the food product. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. After the food product has been immersed for a time sufficient for the desired antimicrobial effect, the food product can be removed from the bath or flume and the compositions can be rinsed, drained, or evaporated off the food product.

In other embodiments, a food product can be treated with a foaming version of the compositions of the present invention. The foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, including, for example, alkyl aryl sulfonates, quaternary ammonium compounds, alkyl sarcosines, betaines and alkyl amides. The foaming surfactant is typically mixed at time of use with the washing solution. Use solution levels of the foaming agents is from about 50 ppm to about 2.0 wt-%. At time of use, compressed air can be injected into the mixture, then applied to the food product surface through a foam application device such as a tank foamer or an aspirated wall mounted foamer.

In some embodiments, a food product can be treated with a thickened or gelled version of the compositions of the present invention. In the thickened or gelled state the washing solution remains in contact with the food product surface for longer periods of time, thus increasing the antimicrobial efficacy. The thickened or gelled solution will also adhere to vertical surfaces. The compositions can be thickened or gelled using existing technologies such as: xanthan gum, polymeric thickeners, cellulose thickeners, or the like. Rod micelle forming systems such as amine oxides and anionic counter ions could also be used. The thickeners or gel forming agents can be used either in the concentrated product or mixing with the washing solution, at time of use. Typical use levels of thickeners or gel agents range from about 100 ppm to about 10 wt-%.

Methods for Beverage, Food, and Pharmaceutical Processing

The compositions of the present invention can be used in the manufacture of beverage, food, and pharmaceutical materials including fruit juice, dairy products, malt beverages, soybean-based products, yogurts, baby foods, bottled water products, teas, cough medicines, drugs, and soft drinks. The compositions of the present invention can be used to sanitize, disinfect, act as a sporicide for, or sterilize bottles, pumps, lines, tanks and mixing equipment used in the manufacture of such beverages. Further, the compositions of the present invention can be used in aseptic, cold filling operations in which the interior of the food, beverage, or pharmaceutical container is sanitized or sterilized prior to filling. In such operations, a container can be contacted with the compositions, typically using a spray, dipping, or filling device to intimately contact the inside of the container with the compositions, for a sufficient period of time to reduce microorganism populations within the container. The container can then be emptied of the amount of sanitizer or sterilant used. After emptying, the container can be rinsed with potable water or sterilized water and again emptied. After rinsing, the container can be filled with the beverage, food, or pharmaceutical. The container can then be sealed, capped or closed and then packed for shipment for ultimate sale. The sealed container can be autoclaved or retorted for added microorganism kill.

In food, beverage, or pharmaceutical manufacturing, fungal microorganisms of the genus *Chaetomium* or *Arthrinium*, and spores or bacteria of the genus *Bacillus* spp. can be a significant problem in bottling processes, particularly in cold aseptic bottling processes. The compositions of the present invention can be used for the purpose of controlling or substantially reducing (by more than a 5 $\log_{10}$ reduction) the number of *Chaetomium* or *Arthrinium* or *Bacillus* microorganisms in beverage or food or pharmaceutical bottling lines using cold aseptic bottling techniques.

In such techniques, metallic, aluminum or steel cans can be filled, glass bottles or containers can be filled, or plastic (PET or PBT or PEN) bottles, and the like can be filled using cold aseptic filling techniques. In such processes, the compositions of the invention can be used to sanitize the interior of beverage containers prior to filling with the carbonated (or noncarbonated) beverage. Typical carbonated beverages in this application include, but are not limited to, cola beverages, fruit beverages, ginger ale beverages, root beer beverages, iced tea beverages which may be non-carbonated, and other common beverages considered soft drinks. The compositions of the invention can be used to sanitize both the tanks, lines, pumps, and other equipment used for the manufacture and storage of the soft drink material and also used in the bottling or containers for the beverages. In an embodiment, the compositions are useful for killing both bacterial and fungal microorganisms that can be present on the surfaces of the production equipment and beverage containers.

Methods for Industrial Processing

In some aspects, the invention includes methods of using the peroxycarboxylic acid forming compositions and/or peroxycarboxylic acids to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, the peroxycarboxylic acid forming compositions and/or peroxycarboxylic acids are used to control the growth of microorganisms in water used in various oil and gas operations. In a further aspect, the compositions are suitable for incorporating into fracturing fluids to control or eliminate microorganisms.

For the various industrial processes disclosed herein, "liquid system" refers to flood waters or an environment within at least one artificial artifact, containing a substantial amount of liquid that is capable of undergoing biological fouling, it includes but is not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In at least one embodiment this technology would be applicable to any process or utility liquid system where microorganisms are known to grow and are an issue, and biocides are added. Examples of some industrial process water systems where the method of this invention could be applied are in process water applications (flume water, shower water, washers, thermal processing waters, brewing, fermentation, CIP (clean in place), hard surface sanitization, etc.), Ethanol/Bio-fuels process waters, pretreatment and utility waters (membrane systems, ion-exchange beds), water used in the process/manufacture of paper, ceiling tiles, fiber board, microelectronics, E-coat or electro deposition applications, process cleaning, oil exploration and energy services (completion and work over fluids, drilling additive fluids, fracturing fluids, flood waters, etc.; oil fields—oil and gas wells/flow line, water systems, gas systems, etc.), and in particular water systems where the installed process equipment exhibits lowered compatibility to halogenated biocides.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference. The invention is further illustrated by the following examples, which should not be construed as further limiting.

All publications and patent applications in this specification are indicative of the level of ordinary skill in the art to which this invention pertains. All publications and patent applications are herein incorporated by reference to the same extent as if each individual publication or patent application was specifically and individually indicated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

A single peracid chemistry (POOA) having the formula set forth in Table 1A was prepared according to the methods and apparatus of the invention at two different flow rates as shown below in Table 1B.

Methods employed used a continuous generated having a reaction manifold as outlined in FIG. 3. In the continuous generation model, peroxyoctanoic acid was generated through the addition of the sugar ester sorbitol octanoate. The sugar ester was added to the oxidizing source, water and caustic for the hydrolysis reaction to occur at an alkaline pH (e.g. above about 12).

TABLE 1A

| Formula | RM | Amt (%) |
|---|---|---|
| ABF POOA | Sorbitan Octanoate - diluted with 15% IPA | 9.4% |
| | $H_2O_2$ 35% | 9.8% |
| | Soft water | 72.0% |
| | NaOH 50% - rayon | 8.8% |
| | Sum | 100.0% |

TABLE 1B

| | low flow | | High Flow | |
|---|---|---|---|---|
| RM | g/min | Wt % | g/min | Wt % |
| Sorbitan | 6 | 7.2% | 22 | 8.9% |
| 35% Peroxide | 5 | 6.0% | 20 | 8.1% |
| Water | 63 | 75.9% | 180 | 72.7% |
| 50% Caustic | 9 | 10.8% | 25.5 | 10.3% |
| Sum | 83 | 100.0% | 247.5 | 100.0% |
| Ave ± σ | | 2.76 ± 0.11 | | 2.82 ± 0.07 |

The results of the generation of a POOA chemistry using the methods and apparatus of the invention demonstrate that peroxyoctanoic acid (POOA) was prepared at approximately 2.8% concentration at two different flow rates (e.g. 83 g/min and 248 g/min). Beneficially, the apparatus and methods of the invention can be used to produce the same high concentration of desired chemistry at increased production rates, providing clear benefits from a production standpoint in order to satisfy a continuous and/or large volume demand for a particular peracid chemistry to be generated according to the invention.

The resultant peracid samples were analyzed using QATM 317: Suppressed Peroxide Titration for Peracids and Hydrogen Peroxide. Samples were not titrated for hydrogen peroxide.

Example 2

A mixed peracid chemistry (POOA/POAA) having the formula set forth in Table 2A was prepared according to the methods and apparatus of the invention at a higher flow rate as shown below in Table 2B. Table 2C shows the reaction time required for the generation each peracid in the mixed peracid chemistry generated.

Methods employed used a continuous generated having a reaction manifold as outlined in FIG. 3. In the continuous generation model, peroxyoctanoic acid and peroxyacetic acid were generated through the addition of the sugar ester sorbitol octanoate and triacetin. The sugar esters were added to the oxidizing source, water and caustic for the hydrolysis reaction to occur at an alkaline pH (e.g. above about 12). For the mixed peracid systems a single reaction manifold was employed (as opposed to a batch apparatus which may employ more than one reaction vessel or manifold). The dosage and mix time of the input reagents were controlled so that both reactions generated intermediates were completed at the same time. The raw starting material feed times varied to ensure the kinetics for the desired peracid system were achieved in a timely manner. As set forth according to the invention, understanding when the perhydrolysis reaction starts is key to calculating reaction time and the dosing of the raw starting materials (e.g. sugar esters). For example; the reaction time starts when the pH of the reaction mixture is increased through the addition of the caustic into the reaction manifold and not when caustic addition is finished.

TABLE 2A

| Formula | RM | Amt (%) |
|---|---|---|
| ABF POOA/POAA | Sorbitan Octanoate | 9.4% |
| | $H_2O_2$ 35% | 9.8% |
| | Soft water | 72.0% |
| | NaOH 50% - rayon | 8.8% |
| | Triacetin | 3.5% |
| | Sum | 100.0% |

TABLE 2B

| | High Flow | |
|---|---|---|
| RM | g/min | Wt % |
| Sorbitan | 28 | 10.4% |
| 35% Peroxide | 21 | 7.8% |
| Water | 183 | 68.3% |
| 50% Caustic | 27 | 10.1% |
| Triacetin | 9 | 3.4% |
| Sum | 268.0 | 100.0% |

TABLE 2C

| | Rxn Time | Wt % |
|---|---|---|
| POOA | 8.4 | 2.82 |
| POAA | 1.1 | 2.58 |

The results show the production of a mixed peracid containing peroxyoctanoic acid (POOA) and peroxyacetic acid (POAA) at 2.8% and 2.6%, respectively, at a production rate of 268 g/min. The results confirm that either a peracid or mixed peracids can be prepared using the perhydrolysis of, for example, sorbitan octanoate and/or triacetin (sugar esters). Notably, additional sugar esters, including those disclosed herein (e.g. glyceryl octanoate) can be substituted the generation of a particular peracid chemistry.

The resultant peracid samples were analyzed using QATM 317: Suppressed Peroxide Titration for Peracids and Hydrogen Peroxide. Samples were not titrated for hydrogen peroxide. Determination of peroctanoic acid and peracetic acid in the mixed peracid sample was obtained by first generating the peroctanoic acid with the triacetin pump turned off and measuring the POOA concentration, sample A. The triacetin pump was then turned on and five minutes were allowed to enable the triacetin-containing mixture to reach the end of the flow manifold. The mixed peracid sample (B) was collected and titrated. The peracetic acid concentration was calculated as B-A.

Example 3

The methods and apparatus according to the invention were tested to obtain increased percentage of peracid. Table 3 shows the peracid chemistry (POOA) generated according to the methods and apparatus of the invention. As shown titrated POOA produced was 5.7% and 5.8% within 5 minutes.

TABLE 3

|  | Formulation Proposed | Desired g/min | Measured g/min | Formulation Evaluated |
|---|---|---|---|---|
| Glycerol octanoate | 14.67% | 15.4 | 16 | 15.3% |
| 35% HP | 19.42% | 20.4 | 22.8 | 21.8% |
| Water | 49.17% | 51.5 | 50 | 47.7% |
| 50% NaOH | 16.74% | 17.5 | 16 | 15.3% |
| Sum | 100.00 | 104.8 | 104.8 | 100% |

The results confirm that peracid concentrated can be generated according to the perhydrolysis of sugar esters according to the invention in amounts exceeding those obtained from equilibrium reactions. In addition, the methods and apparatus generate desired peracids rapidly.

Example 4

Adjustable biocide formulator system operating procedures. A user or process controller input determines the desired peracid formulation and volume to be generated on-site in the continuous generator. Input information is loaded into the formulator system. Formulator software calculates the time required to dose raw materials into reactor(s) and reaction time.

Upon set up, feed pumps are calibrated. Raw materials are fed to reaction vessel(s) and mixed in reaction vessel for a period of time for perhydrolysis reaction to take place. The extent of reaction is measured to determine when to quench a reaction with acid. Acid is either dosed into the reaction manifold at the end of a mix period for short life intermediates or is dosed at a later time for longer lasting intermediates. Upon completion of the perhydrolysis reaction the intermediates may be pumped to a sump reservoir for dosing to a cleaning process or may be dosed directly from reaction vessel into a cleaning process. Beneficially the quenching reaction with the acid may take place within the reaction manifold or outside of the reaction manifold.

Example 5

Rheology of sugar esters. Rheology modifiers may optionally be included in the methods according to the present invention. Water soluble or water dispersible rheology modifiers that are useful can be classified as inorganic or organic. The organic thickeners can further be divided into natural and synthetic polymers with the latter still further subdivided into synthetic natural-based and synthetic petroleum-based.

Additional experimentation demonstrates the best rheology of the ester to increase accuracy.

Example 6

A series of experiments were conducted to determine the impact of the order of addition of reagents on the generation of peracid chemistry using the ABF generator according to the invention. The ABF generator according to the invention has demonstrate efficacy in the production of a peroxyoctanoic acid solutions though combination of pre-cursor chemistries (e.g. ester premix with hydroxide and/or other activators) combined prior to having the reactants enter a reaction vessel. Surprisingly, an aspect of the invention involves the impact of reagent addition order and dilution of the reagents on the generation of peracid chemistry. Aspects of the invention disclose preferred operating methods for generating a consist output (which is non-fouling) from the mixer and reaction vessel.

First, the ABF generator mixed reagents in the following order and design: water, ester/peroxide, NaOH to form peracid. In particular, when the system was activated it injected water, ester/peroxide premix, and 50% caustic into a series of clear PVC injection manifolds that were plumbed together in series. The flow rate for all reagents entering the system was controlled at 25 g/min. Samples of the resultant mixture were collected at the exit of the solution and were titrated using an iodometric titration procedure for peroxyoctanoic acid 10 minutes after the reagents were initially mixed. The resultant titration yielded a peracid concentration of approximately 1.75%. Based on the reagent formulation a POOA concentration of approximately 5.50% was expected. Upon evaluation of the mixing manifold it was apparent that a waxy solid was formed between the ester and NaOH injection ports, providing a rationale for the low POOA titration. In particular, a poor mass transfer through the system resulted from the mix order of the reagents.

The second test order of ABF generator mixed reagents occurred nearly the same as the first example, with the exception that the injection points for the ester/peroxide premix and the NaOH were reversed. In particular, when the system was activated it injected water, 50% caustic and an ester/peroxide premix into a series of clear PVC injection manifolds that were plumbed together in series. The results were the same as those outlined in the first example run of this Experiment 6, showing that under concentration conditions mixing order alone cannot overcome the fouling of the reagents.

The third example, tested the theory that the formation of the solid was a reaction between the concentrated ester and concentrated caustic. This was tested by combining 5 grams of glycerol octanoate with 5 grams of 50% NaOH in a 150 ml beaker. When the 2 materials were mixed they immediately formed a waxy solid that was very difficult to dissolve even in hot (60° C.) water. This test confirmed the importance of dilute the caustic and/or sugar ester premix prior to reaction within the systems according to the invention.

A fourth test was conducted based on the results of the prior tests within this Example 6 to confirm whether an issue with the formation of the solid (e.g. fouled reagents) was poor dispersion of the ester/peroxide premix in the water prior to addition of the caustic. To alleviate this issue an injection manifold was re-designed to pre-mix the ester/peroxide solution with water prior to addition of the NaOH. In particular, an ester/peroxide premix is diluted and mixed within a static mixer prior to the addition of the caustic. Unexpectedly, the premixing of the ester/peroxide and water did not alleviate the precipitation issue (e.g. fouling of the reagents) as a precipitate still formed downstream from the addition of the NaOH. In addition, when titrating the solution a peracid concentration of POOA less than 1.0% was measured.

A fifth test was conducted. The order of addition of the reagents was further modified. In particular, the ester/peroxide premix and NaOH premix injection ports on the injection manifold were switched. In particular, when the system was activated it injected water and 50% caustic, prior to the addition of the ester/peroxide premix into the system. The outcome of this change in mix order of reagents was expected to generate similar or even poorer results relative to those from prior examples as this mixing profile would produce even less dispersion of ester/peroxide. Surprisingly, changing the order of addition had a marked effect on the reaction. Mixing the components in this manner produced a uniform output from the mixing manifold with no precipitation. In addition a sample of the peracid chemistry produced by this modified mixing system titrated a 5.46% peroxyoctanoic acid yield at 10 minutes after the chemistry precursors were combined.

The tests and results demonstrate the importance of the order of addition (e.g. diluted caustic followed by ester/peroxide premix).

Example 7

A series of experiments were conducted to determine the impact of reagent concentration on the generation of peracid chemistry using the ABF generator according to the invention. In particular, the level of NaOH dilution to ensure uniform dispersion of the ester component was further analyzed. As set forth in Table 4, 5 grams of a sugar ester were added to 5 grams of NaOH at varying concentrations—50%, 25%, 20%, 15%, 12.5% and 6.25%. The reagents were added in test tubes with mild agitation. Production of precipitate in this test is an indication that the NaOH dilution is insufficient to produce a uniform output from this system.

TABLE 4

| | NaOH concentration | | | | | |
|---|---|---|---|---|---|---|
| | 50% | 25% | 20% | 15% | 12.5% | 6.25% |
| Ester/ NaOH Rxn | White Solid | White Solid | White solid rapidly dissolves and disperses to a single phase | White solid rapidly dissolves and disperses to a single phase | Turbid single phase | Turbid single phase |

The results shown in Table 4 demonstrate that the adjustable biocide formulator or generator system should deliver a NaOH solution that is no more than 20 wt-% on an actives basis before the ester component is combined with the NaOH to initiate the peracid production reaction.

The inventions being thus described, it will be obvious that the same may be varied in many ways. Such variations are not to be regarded as a departure from the spirit and scope of the inventions and all such modifications are intended to be included within the scope of the following claims.

The invention claimed is:

1. A method of cleaning using an on-site generated peroxycarboxylic acid forming composition comprising:
    obtaining a user- or system-inputted peroxycarboxylic acid forming composition on-site using an adjustable biocide formulator or generator system comprising: an apparatus comprising a variable length of a reaction manifold, a series of feed pumps and an outlet for dosing a peroxycarboxylic acid forming composition from the reaction manifold;
    sequentially or in parallel adding reagents to the reaction manifold to produce a peroxycarboxylic acid forming composition, wherein the reagents comprise: (1) at least one ester of a polyhydric alcohol and a $C_1$ to $C_{18}$ carboxylic acid, (2) a source of alkalinity, and (3) an oxidizing agent; and
    applying the peroxycarboxylic acid forming composition in an amount sufficient to sanitize, bleach and/or disinfect a surface in need thereof,
    wherein the reaction manifold is in fluid connection with the outlet to dispense the peroxycarboxylic acid forming composition;
    wherein the reaction manifold is a length of tubing having multiple points of input via at least one injection manifold wherein the feed pumps provide the reagents for the continuous production of the peroxycarboxylic acid forming composition;
    wherein the feed pumps are in fluid connection with the reaction manifold and supply the reagents to produce the peroxycarboxylic acid forming composition in the reaction manifold;
    wherein the peroxycarboxylic acid forming composition is an individual or mixed peroxycarboxylic acid forming composition according to a user- or system-inputted selection.

2. The method according to claim 1, wherein the reagents comprise a first ester of a polyhydric alcohol and a $C_1$ to $C_{18}$ carboxylic acid, and a second ester of a polyhydric alcohol and a $C_1$ to $C_{18}$ carboxylic acid.

3. The method according to claim 2, wherein the first ester of a polyhydric alcohol and a $C_1$ to $C_{18}$ carboxylic acid comprises sorbitan octanoate and/or glyceryl octanoate, and the second ester of a polyhydric alcohol and a $C_1$ to $C_{18}$ carboxylic acid comprises triacetin.

4. The method according to claim 2, wherein the sequential or parallel addition of the reagents to the reaction manifold produces a mixed peroxycarboxylic acid forming composition.

5. The method according to claim 1, wherein the source of alkalinity is an alkaline metal hydroxide, an alkaline earth metal hydroxide, an alkali metal silicate, an alkali metal carbonate, borates and mixtures thereof, and wherein the source of alkalinity is provided to the reaction vessel prior to the addition of the at least one ester of a polyhydric alcohol and a $C_1$ to $C_{18}$ carboxylic acid in a solution that is less than about 20 wt-% source of alkalinity on an actives basis.

6. The method according to claim 1, wherein the oxidizing agent is a hydrogen peroxide donor.

7. The method according to claim 1, wherein the apparatus further comprises at least one measurement device, wherein the at least one measurement device measures one or more reaction kinetics or system operations for the peroxycarboxylic acid forming composition generation, and wherein the at least one measurement device measures fluorescence, weight, flow, capacitive level, pH, oxidation reduction potential, pressure, temperature and combinations thereof.

8. The method according to claim 1, wherein the apparatus further comprises a reservoir in fluid connection with the reaction manifold outlet to mix or store the peroxycarboxylic acid forming compositions from the reaction manifold.

9. The method according to claim 1, wherein the apparatus further comprises a cooling system on the reaction manifold, wherein the cooling system is a quenching node, a reaction manifold with an increased surface area, a cooling jacket, a venting system, a cold finger, and combinations thereof.

10. The method according to claim 1, wherein the apparatus further comprises a flow meter.

11. The method according to claim 10, wherein the feed pumps provide the reagents by tick on the flow meter.

12. The method according to claim 1, wherein the apparatus further comprises a control software for operating the apparatus to generate a user- or system-inputted peroxycarboxylic acid forming composition and desired volume of the peroxycarboxylic acid forming composition for on-site generation.

13. The method according to claim 12, wherein the control software determines the timing of feeding the reagents to the reaction manifold, mixing and reaction time required for production of the user- or system-inputted peroxycarboxylic acid forming composition and desired volume.

14. The method according to claim 1, further comprising a data output means for sharing information related to the peroxycarboxylic acid forming composition formulation, peroxycarboxylic acid forming composition consumption or usage, additional peroxycarboxylic acid forming composition production-related data or combinations of the same.

15. A method of cleaning textiles using an on-site generated peroxycarboxylic acid forming composition comprising:

obtaining a user- or system-inputted peroxycarboxylic acid forming composition on-site using an adjustable biocide formulator or generator system comprising: an apparatus comprising a variable length of a reaction manifold, a series of feed pumps and an outlet for dosing a peroxycarboxylic acid forming composition from the reaction manifold;

sequentially adding reagents to the reaction manifold to produce a peroxycarboxylic acid forming composition, wherein the reagents comprise: (1) one or more esters of a polyhydric alcohol and a $C_1$ to $C_{18}$ carboxylic acid, (2) a source of alkalinity, and (3) an oxidizing agent at alkaline pH in the adjustable biocide formulator or generator system at a pH above at least 12; and applying the peroxycarboxylic acid forming composition in an amount sufficient to sanitize, bleach and/or disinfect a surface in need thereof, wherein the reaction manifold is in fluid connection with the outlet to dispense the peroxycarboxylic acid forming composition;

wherein the reaction manifold is a length of tubing having multiple points of input via at least one injection manifold wherein the feed pumps provide the reagents for the continuous production of the peroxycarboxylic acid forming composition;

wherein the feed pumps are in fluid connection with the reaction manifold and supply the reagents to produce the peroxycarboxylic acid forming composition in the reaction manifold;

wherein the peroxycarboxylic acid forming composition is an individual or mixed peroxycarboxylic acid forming composition according to a user- or system-inputted selection.

16. The method according to claim 15, further comprising supplying the peroxycarboxylic acid forming composition to a tunnel washer of a wash machine.

17. The method according to claim 16, wherein the peroxycarboxylic acid forming composition is diluted to form a use solution.

18. The method according to claim 17, further comprising a step of applying the use solution to laundry or textile surfaces in the tunnel washer.

19. The method according to claim 18, wherein the laundry or textile surfaces are wetted by the use solution for a sufficient time to wash, destain, sanitize, bleach, and/or rinse the laundry or textile surfaces.

20. The method according to claim 15, further comprising a post-generator acidification step comprising adding a peroxycarboxylic acid as a sanitizer.

* * * * *

UNITED STATES PATENT AND TRADEMARK OFFICE
CERTIFICATE OF CORRECTION

PATENT NO. : 11,311,011 B2
APPLICATION NO. : 16/232681
DATED : April 26, 2022
INVENTOR(S) : Paul R. Kraus et al.

It is certified that error appears in the above-identified patent and that said Letters Patent is hereby corrected as shown below:

In the Specification

In Column 1, Line 18:
DELETE "is a continuation-in-part of"
INSERT --claims the benefit of--.

Signed and Sealed this
Fifth Day of July, 2022

Katherine Kelly Vidal
Director of the United States Patent and Trademark Office